(12) United States Patent
Waterman et al.

(10) Patent No.: US 7,413,873 B2
(45) Date of Patent: Aug. 19, 2008

(54) METHOD OF DETECTION AND TREATMENT OF COLON CANCER

(75) Inventors: Marian L. Waterman, Irvine, CA (US); Randall F. Holcombe, Coto de Caza, CA (US); J. Lawrence Marsh, Newport Beach, CA (US); Karine Hovanes, Westminster, CA (US); Tony Wai Hung Li, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 576 days.

(21) Appl. No.: 10/134,092

(22) Filed: Apr. 25, 2002

(65) Prior Publication Data

US 2002/0187502 A1 Dec. 12, 2002

Related U.S. Application Data

(63) Continuation-in-part of application No. 10/060,844, filed on Jan. 29, 2002, now abandoned.

(60) Provisional application No. 60/265,264, filed on Jan. 30, 2001.

(51) Int. Cl.
C12N 15/00 (2006.01)
(52) U.S. Cl. .................... 435/69.1; 536/23.1; 435/320.1
(58) Field of Classification Search .................. 536/23.1
See application file for complete search history.

(56) References Cited

OTHER PUBLICATIONS

Hsu et al (1998, Molecular and Cellular Biology, vol. 18, No. 8, pp. 4807-4818).*
NCBI accession No. AF198532 (PRI Nov. 25, 1999).*
Hovanes et al., (May 2001, Nature Genetics, vol. 28, pp. 53-57).*
Waterman et al., Genes Dev. Apr. 1991;5(4):656-69.*
Voet et al., (Biochemistry, John Wiley & Sons, 1990, pp. 835-837 only).*
The sequence alignment of GenEmbl Accession No. AF288571 (Aug. 20, 2000, Hovanes et al) against nucleotides 999-1854 of the instant SEQ ID No. 3.*
The sequence alignment of GenEmbl Accession No. AF288571 (Aug. 20, 2000, Hovanes et al) aginst a polynucleotide encoding the instant SEQ ID No. 5.*
The sequence alignment of GenEmbl Accession No. AP002077 (Aug. 10, 2000) against nucleotides 153-201 of SEQ ID No. 1.*
The sequence alignment of GenEmbl Accession No. AF198532 (Nov. 25, 1999) against a polynucleotide encoding the instant SEQ ID No. 5.*
Bienz and Clevers, "Linking Colorectal Cancer to Wnt Signaling", Cell, vol. 103, pp. 311-320, 2000.
Cadigan, Kenneth M. et al., "Wingless Repression of Drosophila frizzled 2 Expression Shapes the Wingless Morphogen Gradient in the Wing", Cell, vol. 93, pp. 767-777, 1998.

Groden, Joanna et al., "Identificationa nd Characterization of the Familial Adenomatous Polyposis Coli Gene", Cell, vol. 66, pp. 589-600, 1991.
Heslip, Tim R. et al., "Shaggy and Dishevelled exert opposite effects on wingless and decapentaplegic expression and non positional identity in imaginal discs", Developmentl, vol. 124, pp. 1069-1078, 1997.
Hirsinger, Estelle et al., "Noggin acts downstream of Wnt and Sonic Hedgehog to antagonize BMP4 in avian somite patterning", Development, vol. 124, pp. 4605-4614, 1997.
Hooper, Joan E., "Distinct pathways for autocrine and paracrine Wingless signalling Drosophila embryos", Nature, vol. 372, 1994.
Hovanes, K et al., "The human LEF-1 gene contains a promoter preferentially active in lymphocytes and encodes multiple isoforms derived from alternative splicing", Nucleic Acids Research, vol. 28, pp. 1994-2003, 2000.
Kinzler, Kenneth W. et al, "Identification of FAP Locus Genes from Chromosome 5q21", Reports, pp. 661-665, 1991.
Korinek, Vladimir et al., "Constitutive Transcriptional Activation by a β-Catenin-Tcf Complex in APC$^{-/-}$ Colon Carcinoma", Science, vol. 275, pp. 1784-1787, 1997.
Molenaar, Miranda et al., "XTcf-3 Transcription Factor Mediates β-Catenin-Induced Axis Formation in Xenopus Embryos", Science, vol. 280, pp. 1564-1569, 1998.
Noordermeer, Jasprien et al., "The consequences of ubiquitous expression of the wingless gene in the Drosophila embryo", Development, vol. 116, pp. 711-719, 1992.
Polakis, Paul, "Wnt signaling and cancer", Genes & Dev., vol. 14, pp. 1837-1851, 2000.
Prieve and Waterman, "Nuclear Localization and Formation of β-Catenin-Lymphoid Enhancer Factor 1 Comlexes Are Not Sufficient for Activation of Gene Expression", Molecular and Cellular Biology, vol. 19, No. 6, pp. 4503-4515, 1999.
Riggins, Greogry J. et al., "Mad-related genes in the human", Nature Genetics, vol. 13, pp. 461-464, 1996.
Roose, Jeroen et al., "Synergy Between Tumor Suppressor APC and the β-Catenin-Tcf4 Target Tcf1", Science, vol. 285, pp. 1923-1926, 1999.
Theisen, Heidi et al., "Developmental territories created by mutual antagonism between Wingless and Decapentaplegic", Development, vol. 122, pp. 3939-3948, 1996.
Van de Wetering, Marc et al., "Extensive Alternative Splicing and Dual Promoter Usage Generate Tcf-1 Protein Isoforms with Differential Transcription Control Properties", Molecular and Cellular Biology, vol. 16, No. 3, pp. 745-752, 1996.

* cited by examiner

Primary Examiner—Misook Yu
(74) Attorney, Agent, or Firm—DLA Piper US LLP

(57) ABSTRACT

The present invention is based, in part, on the discovery that colon carcinoma, carcinogenesis, or the predisposition thereto is associated with the level of Wnt2, Wnt5, BMP6, and Fz receptors and the full-length and dominant negative form of LEF1.

16 Claims, 4 Drawing Sheets

SEQUENCE LISTING

<160> NUMBER OF SEQ ID NOS: 4

<210> SEQ ID NO 1
<211> LENGTH: 3084
<212> TYPE: DNA
<213> ORGANISM: Homo sapiens

<400> SEQUENCE: 1

```
aagatctaaa aacggacatc tccaccgtgg gtggctcctt tttcttttc ttttttccc       60 acccttcagg aagtggacgt ttcgttatct tctgatcctt gcaccttctt ttgggggaaac    120 ggggcccttc tgcccagatc ccctctcttt tctcggaaaa caaactacta agtcggcatc    180
cggggtaact acagtggaga gggtttccgc ggagacgcgc cgccggaccc tcctctgcac    240
```

```
tttggggagg cgtgctccct ccagaaccgg cgttctccgc gcgcaaatcc cggcgacgcg    300
gggtcgcggg gtggccgccg gggcagcctc gtctagcgcg cgccgcgcag acgccccgg    360
agtcgccagc taccgcagcc ctcgccgccc agtgccnttc ggcctcgggg cgggcgcctg    420
cgtcggtctc cgcgaagcgg gaaagcgcgg cggccgccgg gattcgggcg ccgcggcagc    480
tgctccggct gccggccggc ggccccgcgc tcgcccgccc cgcttccgcc cgctgtcctg    540
ctgcacgaac ccttccaact ctcctttcct cccccaccct tgagttaccc ctctgtcttt    600
cctgctgttg cgcgggtgct cccacagcgg agcggagatt acagagccgc cgggatgccc    660
caactctccg gaggaggtgg cggcggcggg ggggaccccgg aactctgcgc cacgacgag    720
atgatcccct tcaaggacga gggcgatcct cagaaggaaa agatcttcgc cgagatcagt    780
catcccgaag aggaaggcga tttagctgac atcaagtctt ccttggtgaa cgagtctgaa    840
atcatcccgg ccagcaacgg acacgaggtg ccagacaag cacaaacctc tcaggagccc    900
taccacgaca aggccagaga acaccccgat gacggaaagc atccagatgg aggcctctac    960
aacaagggac cctcctactc gagttattcc gggtacataa tgatgccaaa tatgaataac   1020
gacccataca tgtcaaatgg atctcttttct ccacccatcc cgagaacatc aaataaagtg   1080
cccgtggtgc agccatccca tgcggtccat cctctcaccc ccctcatcac ttacagtgac   1140
gagcactttt ctccaggatc acacccgtca cacatcccat cagatgtcaa ctccaaacaa   1200
ggcatgtcca gacatcctcc agctcctgat atccctactt tttatcccct tgtctccgggt   1260
ggtgttggac agatcacccc acctcttggc tggcaaggtc agcctgtata tcccatcacg   1320
ggtggattca ggcaacccta cccatcctca ctgtcagtcg acacttccat gtccaggttt   1380
tcccatcata tgattcccgg tcctcctggt cccacacaa ctggcatccc tcatccagct   1440
attgtaacac ctcaggtcaa acaggaacat ccccacactg acagtgacct aatgcacgtg   1500
aagcctcagc atgaacagag aaaggagcag gagccaaaaa gacctcacat taagaagcct   1560
ctgaatgctt ttatgttata catgaaagaa atgagagcga atgtcgttgc tgagtgtact   1620
ctaaaagaaa gtgcagctat caaccagatt cttggcagaa ggtggcatgc cctctcccgt   1680
gaagagcagg ctaaatatta tgaattagca cggaaagaaa gacagctaca tatgcagctt   1740
tatccaggct ggtctgcaag agacaattat ggtaagaaaa agaagaggaa gagagagaaa   1800
ctacaggaat ctgcatcagg tacaggtcca agaatgacag ctgcctacat ctgaaacatg   1860
gtggaaaacg aagctcattc ccaacgtgca aagccaaggc agcgacccca ggacctcttc   1920
tggagatgga agcttgttga aacccagac tgtctccacg gcctgccag tcgacgccaa   1980
aggaacactg acatcaattt taccctgagg tcactgctag agacgctgat ccataaagac   2040
aatcactgcc aaccccctct tcgtctactg caagagccaa gttccaaat aaagcataaa   2100
aaggtttttt aaaaggaaat gtaaaagcac atgagaatgc tagcaggctg tggggcagct   2160
gagcagcttt tctcccccca tatctgcgtg cacttcccag agcatcttgc atccaaacct   2220
gtaacctttc ggcaaggacg gtaacttggc tgcatttgcc tgtcatgcgc aactggagcc   2280
agcaaccagc tatccatcag caccccagtg gaggagttca tggaagagtt ccctctttgt   2340
ttctgcttca tttttctttc ttttcttttc tcctaaagct tttatttaac agtgcaaaag   2400
gatcgttttt ttttgctttt ttaaacttga attttttttaa tttacacttt ttagttttaa   2460
ttttcttgta tattttgcta gctatgagct tttaaataaa attgaaagtt ctggaaaagt   2520
ttgaaataat gacataaaaa gaagccttct ttttctgaga cagcttgtct ggtaagtggc   2580
ttctctgtga attgcctgta acacatagtg gcttctccgc ccttgtaagg tgttcagtag   2640
```

-continued

```
agctaaataa atgtaatagc caaaccccac tctgttggta gcaattggca gccctatttc    2700
agtttatttt ttcttctgtt ttcttctttt cttttttaa acagtaaacc ttaacagatg    2760
cgttcagcag actggtttgc agtgaatttt catttctttc cttatcaccc ccttgttgta    2820
aaaagcccag cacttgaatt gttattactt taaatgttct gtatttgtat ctgtttttat    2880
tagccaatta gtgggatttt atgccagttg ttaaaatgag cattgatgta cccattttt     2940 aaaaaagcaa gcacagcctt tgcccaaaac tgtcatccta acgtttgtca ttccagtttg    3000
agttaatgtg ctgagcattt ttttaaaaga agctttgtaa taaaacattt ttaaaaattg    3060
tcatttaaaa aaaaaaaaaa aaaa                                          3084
```

<210> SEQ ID NO 2
<211> LENGTH: 399
<212> TYPE: PRT
<213> ORGANISM: Homo sapiens

<400> SEQUENCE: 2

```
Met Pro Gln Leu Ser Gly Gly Gly Gly Gly Gly Gly Asp Pro Glu
1               5                   10                  15

Leu Cys Ala Thr Asp Glu Met Ile Pro Phe Lys Asp Glu Gly Asp Pro
            20                  25                  30

Gln Lys Glu Lys Ile Phe Ala Glu Ile Ser His Pro Glu Glu Glu Gly
        35                  40                  45

Asp Leu Ala Asp Ile Lys Ser Ser Leu Val Asn Glu Ser Glu Ile Ile
    50                  55                  60

Pro Ala Ser Asn Gly His Glu Val Ala Arg Gln Ala Gln Thr Ser Gln
65                  70                  75                  80

Glu Pro Tyr His Asp Lys Ala Arg Glu His Pro Asp Asp Gly Lys His
                85                  90                  95

Pro Asp Gly Gly Leu Tyr Asn Lys Gly Pro Ser Tyr Ser Ser Tyr Ser
            100                 105                 110

Gly Tyr Ile Met Met Pro Asn Met Asn Asn Asp Pro Tyr Met Ser Asn
        115                 120                 125

Gly Ser Leu Ser Pro Pro Ile Pro Arg Thr Ser Asn Lys Val Pro Val
    130                 135                 140

Val Gln Pro Ser His Ala Val His Pro Leu Thr Pro Leu Ile Thr Tyr
145                 150                 155                 160

Ser Asp Glu His Phe Ser Pro Gly Ser His Pro Ser His Ile Pro Ser
                165                 170                 175

Asp Val Asn Ser Lys Gln Gly Met Ser Arg His Pro Pro Ala Pro Asp
            180                 185                 190

Ile Pro Thr Phe Tyr Pro Leu Ser Pro Gly Gly Val Gly Gln Ile Thr
        195                 200                 205

Pro Pro Leu Gly Trp Gln Gly Gln Pro Val Tyr Pro Ile Thr Gly Gly
    210                 215                 220

Phe Arg Gln Pro Tyr Pro Ser Ser Leu Ser Val Asp Thr Ser Met Ser
225                 230                 235                 240

Arg Phe Ser His His Met Ile Pro Gly Pro Pro Gly Pro His Thr Thr
                245                 250                 255

Gly Ile Pro His Pro Ala Ile Val Thr Pro Gln Val Lys Gln Glu His
            260                 265                 270

Pro His Thr Asp Ser Asp Leu Met His Val Lys Pro Gln His Glu Gln
        275                 280                 285
```

-continued

```
Arg Lys Glu Gln Glu Pro Lys Arg Pro His Ile Lys Lys Pro Leu Asn
    290                 295                 300

Ala Phe Met Leu Tyr Met Lys Glu Met Arg Ala Asn Val Val Ala Glu
305                 310                 315                 320

Cys Thr Leu Lys Glu Ser Ala Ala Ile Asn Gln Ile Leu Gly Arg Arg
                325                 330                 335

Trp His Ala Leu Ser Arg Glu Glu Gln Ala Lys Tyr Tyr Glu Leu Ala
            340                 345                 350

Arg Lys Glu Arg Gln Leu His Met Gln Leu Tyr Pro Gly Trp Ser Ala
        355                 360                 365

Arg Asp Asn Tyr Gly Lys Lys Lys Arg Lys Arg Glu Lys Leu Gln
    370                 375                 380

Glu Ser Ala Ser Gly Thr Gly Pro Arg Met Thr Ala Ala Tyr Ile
385                 390                 395

<210> SEQ ID NO 3
<211> LENGTH: 284
<212> TYPE: DNA
<213> ORGANISM: Homo sapiens
<220> FEATURE:
<221> NAME/KEY: CDS
<222> LOCATION: (267)..(284)

<400> SEQUENCE: 3
atctggtttg ctgctaagct atttaagaga ataaatactg tcaatctaaa atagagcata      60
ataatccagt tacagtattt tgtaaacaaa tcttttatgt agggtctgat ttatcttaga     120
actattagat tttcagatga aaaatacagt aatataaaag ggaagtcagt gcatcattga     180
ttgttctttg gatcttccca ggaaagcatc cagatggagg cctctacaac aagggaccct     240
cctactcgag ttattccggg tacata atg atg cca aat atg aat                  284
                              Met Met Pro Asn Met Asn
                              1               5

<210> SEQ ID NO 4
<211> LENGTH: 6
<212> TYPE: PRT
<213> ORGANISM: Homo sapiens

<400> SEQUENCE: 4

Met Met Pro Asn Met Asn
1               5
```

METHOD OF DETECTION AND TREATMENT OF COLON CANCER

CROSS REFERENCE TO RELATED APPLICATIONS

This application is a continuation-in-part of U.S. Ser. No. 10/060,844 filed on Jan. 29, 2002 now abandoned, which claims priority under 35 U.S.C. 119(e) to U.S. Provisional Application Ser. No. 60/265,264, filed on Jan. 30, 2001, all of which are incorporated herein by reference.

ACKNOWLEDGEMENT OF GOVERNMENT INTEREST

This invention was made in part with government support under Grant No. HD36081, HD36049, CA-83982, and CA82450 awarded by the National Institutes of Health (NIH). The government may have certain rights in this invention.

FIELD OF THE INVENTION

This invention relates generally to the field of colon cancer prognosis, diagnosis, and treatment, especially in association with Wnt signaling pathway including Wnts and their receptors, and β-catenin-sensitive isoforms of lymphoid enhancer factor-1 (LEF-1).

BACKGROUND OF THE INVENTION

Ectopic activation of the Wnt signaling pathway leads to increased cellular growth and division in experimental organisms and mutations in Wnt pathway genes are tightly linked to the genesis of certain cancers in humans (Polakis P., *Genetics & Development*, 9:15-21(1999)). Signaling through the Wnt pathway begins with a Wnt ligand, one of a family of at least 16 members in mammals. (Cadigan K. M., et al., *Genes & Development*, 11:3286-3305 (1997)). Wnts are secreted growth factors that signal through cell surface Frizzled (Fz) transmembrane receptors to initiate the signal cascade (Bhanot P., et al., *Nature*, 282:225-30 (1996); Yang-Snyder J, et al., *Current Biol.*, 6:1302-06 (1996); and He X, et al., *Science*, 275:1652-54 (1997)).

Members of the Dishevelled (Dsh) family are activated upon ligand binding to Fz (Klingensmith J, et al., *Genes Dev.*, 8:118-30 (1994)) causing inhibition of glycogen synthase kinase-3β (GSK-3β, Zw3, shaggy). Inhibition of GSK-3β activity prevents phosphorylation of β-catenin (Armadillo, Arm) thus blocking APC- and Axin-mediated degradation of β-catenin. Stabilized β-catenin accumulates and binds to members of the lymphoid enhancer factor/T-cell factor (LEF/TCF) family of HMG-box transcription factors in the nucleus (Behrens J, et al., *Nature*, 382:638-42 (1996); Van de Wetering M., et al., *Cell*, 88:789-99 (1997); Riese J., et al., *Cell*, 88:777-87 (1997) and Brannon M, et al., *Genes Dev.*, 11:2359-70 (1997) leading to changes in the transcription of growth regulatory genes.

Targets of Wnt-LEF/TCF-regulated transcription include the protooncogene myc (He T. C., et al., *Science*, 281:1509-12 (1998)), cyclooxygenase-2 (COX-2) (Howe L R, et al., *Cancer Res.*, 59:1572-77 (1999)), Matrilysin/MMP-7 (Crawford H. C., et al., *Oncogene*, 18:2883-91 (1999) and Brabletz T., et al., *Am J Pathol.*, 155:1033-38 (1999), cyclin D1 (Testu O., et al., *Nature*, 398:422-26 (1999) and Stutman M., et al., *PNAS*, 96:5522-27 (1999) and a member of the LEF/TCF family, TCF1 (Roose J., et al., *Science*, 285:1923-26 (1999)). Activation of the Wnt pathway also affects the expression of members of another signaling family of molecules, e.g. BMP6 (Bone Morphogenetic Protein), a member of the transforming growth factor (TGF)-β superfamily (Raid M., et al., *Int J Cancer*, 83:38-44 (1999)).

The role of Wnt signaling in cancer was suggested by the discovery that ectopic expression of mouse Wnt1 (int1) caused the formation of mammary tumors in mice (Nusse R., et al., *Cell*, 31:99-109 (1982)). Recognition that the APC (adenomatous polyposis coli) tumor suppressor gene functions as a component of the Wnt pathway further implicated Wnt signaling in cancer, particularly colon cancer (Bienz M., et al., *Cell*, 103:311-20 (2000)). APC mutations (or mutations in β-catenin or axin) are found in up to 85% of sporadic forms of colon cancers (Miyoshi Y., et al., *Hum Mol Genet.*, 1:229-33 (1992) and Potter J. D., *J Nat'l Cancer Inst.*, 91:916-32 (1999)).

Studies in model organisms suggest that the expression of the Wnt genes is controlled by a complex network that employs both positive and negative feedback (Brook W. J., et al., *Science*, 273: 1373-77 (1996) and Theisen H., et al., *Development*, 122:3939-48 (1996)). If true in man, loss of heterozygosity or mutational change of certain members of the Wnt signaling pathway, e.g. APC or β-catenin, might be expected to alter the expression of upstream genes such as those for pathway ligands or receptors. Vider et al. reported (Vider B-Z, et al., *Oncogene*, 12:153-58 (1996)) that Wnt2 is expressed at low levels in normal colon but is overexpressed in tumor tissue samples and that Wnt5a was expressed in both nontumorous as well as colonic tumor tissue, though the methodology used did not distinguish between changes in cancer cells themselves and cells derived from surrounding tissues.

The differential expression of downstream components of the Wnt signaling pathway, specifically members of the LEF/TCF family, has also been suggested. For example, TCF4 is normally expressed in colonic mucosa and cancer (Korinek V., et al., *Science*, 275:1784-87 (1997)) TCF1 is overexpressed in colon cancer cell lines (Meyer K., et al., *Int J Cancer*, 72:625-30 (1997)).

SUMMARY OF THE INVENTION

The present invention is based on the discovery that factors of the Wnt signaling pathway are associated with colon carcinogenesis and can be useful for prognosis, diagnosis, or treatment of colon cancer. Accordingly, the present invention provides isolated polynucleotides and polypeptides of truncated lymphoid enhancer factor-1 (LEF-1) and methods of using the truncated LEF-1 and other agents such as Wnt2, Wnt5, BMP6, and Fz receptors for the detection and treatment of colon cancer.

In one embodiment, the present invention provides an isolated polypeptide containing an amino acid sequence encoding the dominant negative form of LEF1. The present invention also provides polynucleotides encoding the isolated polypeptide, antibodies that specifically bind to the isolated polypeptide, and vectors and cells containing an isolated polynucleotide of the present invention.

In another embodiment, the invention provides a method for detecting colon carcinoma, carcinogenesis or the predisposition thereto. The method includes detecting the level of the full-length LEF1 or the dominant negative form of LEF1 in a sample from a subject, wherein an increase in the level of the full-length or a decrease in the level of the dominant negative form of LEF1 as compared to the level in a subject not having colon carcinoma, is indicative of colon carcinoma or carcinogenesis or the predisposition thereto in the subject.

In yet another embodiment, the present invention provides a kit useful for detecting colon carcinoma, carcinogenesis, or predisposition thereto. The kit comprises a probe, e.g., a nucleic acid probe or an antibody probe for detecting the level of the full-length LEF1 or the dominant negative form of LEF1 and an instruction.

In still another embodiment, the present invention provides a method for inhibiting LEF1 activity in a cell. The method comprises contacting the cell with the isolated polypeptide of the present invention or its encoding polynucleotide thereby inhibiting LEF1 activity in the cell.

In another embodiment, the present invention provides a method for treating colon carcinoma or carcinogenesis. The method includes administering to a subject in need of such treatment an agent, wherein the agent decreases the level of the full-length LEF1 or increases the level of the dominant negative form of LEF1 thereby treating colon carcinoma or carcinogenesis.

In another embodiment, the present invention provides a method for screening for an agent useful for the treatment of colon carcinoma or carcinogenesis. The method includes contacting a test agent with a promoter for the full-length LEF1 or the dominant negative form of LEF1, detecting the activity of the promoter, wherein a test agent decreases the activity of the promoter for the full-length LEF1 or increases the activity of the promoter for the dominant negative form of LEF1 as compared to the activity of the promoter in the absence of the test agent is indicative of an agent useful for the treatment of colon carcinoma or carcinogenesis.

In yet another embodiment, the present invention provides a method for screening for an agent useful for the treatment of colon carcinoma or carcinogenesis. The method includes contacting a test agent with a cell, detecting the level of the full-length LEF1 and the dominant negative form of LEF1, wherein a test agent decreases the level of the full-length LEF1 or increases the level of the dominant negative form of LEF1 as compared to the level in the cell in the absence of the test agent is indicative of an agent useful for the treatment of colon carcinoma or carcinogenesis.

In another embodiment, the present invention provides a method for detecting colon carcinoma, carcinogenesis or the predisposition thereto. The method includes detecting the level of Wnt 2 or Wnt 5 in a sample from a subject, wherein an increase in the level of Wnt 2 or Wnt 5 as compared to the level in a subject not having colon carcinoma is indicative of colon carcinoma, carcinogenesis or the predisposition thereto in the subject.

In yet another embodiment, the present invention provides a method for prognosticating colon carcinoma. The method includes detecting the level of a Fz receptor in a colon carcinoma, wherein a detectable level of Fz receptor is indicative of a poorer prognosis of the colon carcinoma as compared to the prognosis of a colon carcinoma having no detectable level of Fz receptor.

In still another embodiment, the present invention provides a method for detecting colon carcinoma, carcinogenesis or the predisposition thereto. The method includes detecting the level of BMP6 in a sample from a subject, wherein a decrease in the level of BMP6 as compared to the level in a subject not having colon carcinoma is indicative of colon carcinoma, carcinogenesis or the predisposition thereto in the subject.

SUMMARY OF THE FIGURES

FIGS. 2A and 2B show that LEF1 produces two different protein products that differ at the N-terminus. FIG. 2A shows predicted LEF1 protein products from the 3.6 and 2.2 kb mRNAs. The shorter LEF1 protein begins at amino acid 116 within the full length LEF1 sequence and is missing the β-catenin binding domain and a portion of the context-dependent activation domain. FIG. 2B shows that LEF1$^{DN}$ can repress activation of reporter gene expression by β-catenin. The LEF/TCF reporter plasmid TOPtk was co-transfected into 2017 T lymphocytes with increasing amounts of an expression vector for ΔNLEF, a truncated form of LEF1 similar in structure to LEF1$^{DN}$ (aa67-399) (ref. 22). Endogenous LEF/TCFs in Jurkat cells are able to work with β-catenin to activate the reporter gene 15-fold, but in the presence of ΔNLEF1, activation is reduced to basal levels.

FIG. 3A shows predicted LEF1 protein products from the 3.6 and 2.2 kb mRNAs. The shorter LEF1 protein begins at amino acid 116 within the full length LEF1 sequence and is missing the b-catenin binding domain and a portion of the context-dependent activation domain.

FIGS. 4A, 4B, 4C and 4D show that the LEF1 promoter is activated by TCF-1 and TCF4-β-catenin complexes in 2017 T lymphocytes.

Figure 4:
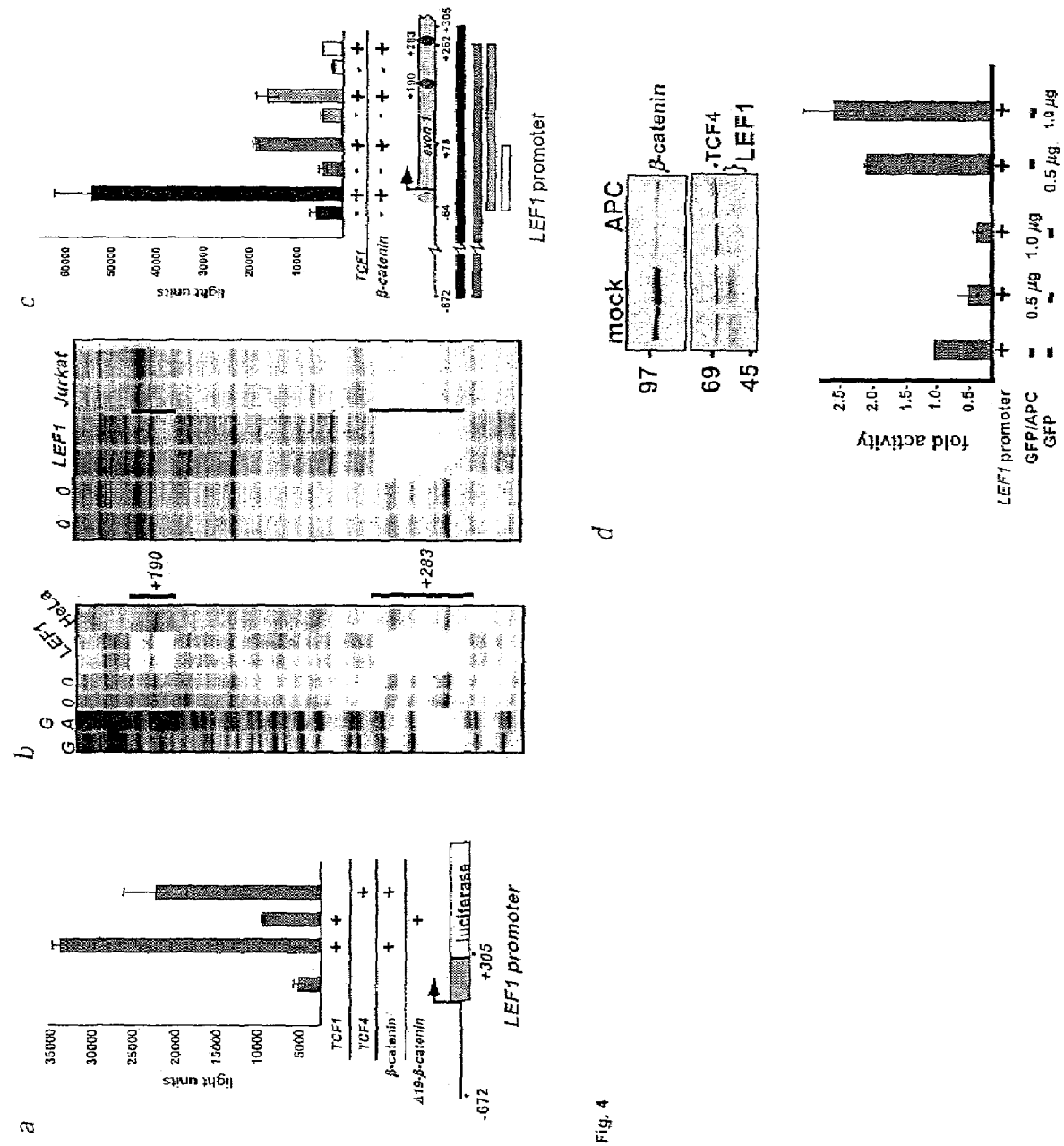

FIG. 4A shows that a luciferase reporter gene driven by the LEF1 promoter (−672, +305) was co-transfected with expression vectors for full length TCF1 or TCF4 and β-catenin. Activation was calculated using equivalent amounts of empty expression vector. TCF1 activated luciferase gene expression 7.0-fold and TCF4 activated 4.6-fold in this representative experiment. Fold activation by TCF1 over 5 replicate experiments is 8±3.65 (SD), for TCF4, 5.6-fold±3.7 (SD). Co-transfection of TCF1 and Δ19 β-catenin, a mutant that cannot bind to LEF/TCF proteins, did not activate the promoter.

FIG. 4B shows DNAase I footprint analysis of the LEF1 promoter with recombinant LEF1 protein reveals two binding sites downstream of the start site of transcription. The footprints are centered over two close matches to LEF/TCF consensus binding sites. A fast migrating portion of intact probe obscures the +1.90 footprint with LEF1 protein in the second panel. Whole cell extracts from Jurkat T lymphocytes (express TCF4, TCF1 and LEF1) but not HeLa cells (little to no LEF/TCF expression) protect the +283 site but not the +190 site.

FIG. 4C shows that fragments of the LEF1 promoter were cloned into pGL2-enhancer plasmids and tested for activation by TCF1 and β-catenin. The region responsive to TCF/β-catenin encompasses the downstream LEF/TCF binding sites. Activation of the largest fragment (−672, +305) was 9.2-fold, whereas activation of fragments that delete the +283 LEF/TCF binding site with (−672, +262) or without (−64, +262) the upstream sequences are activated 4.3- and 3.6-fold respectively. Removal of both the +190 and +283 binding sites (to +78) reduces activation to 1.6-fold.

FIG. 4D shows that transient overexpression of a GFP/APC fusion protein in SW480 cells reduces LEF1 promoter reporter gene activity (−672, +305) three-fold. The parent construct which expresses only the GFP portion does not inhibit promoter activity. Whole cell extracts from Colo320 cells overexpressing GFP/APC were analyzed by western analysis with β-catenin monoclonal antisera, and LEF/TCF polyclonal antisera (75,000 cell equivalents; inset). A decrease in β-catenin and LEF1 levels is observed, but not a decrease in TCF4 levels (indicated by filled circle).

DESCRIPTION OF THE PREFERRED EMBODIMENTS

The present invention relates in general to Wnt signaling pathway and its association with neoplasia, especially colon carcinoma, carcinogenesis or the predisposition thereto. The present invention is based, in part, on the discovery that factors from the upstream and downstream of Wnt singaling pathway, e.g., Wnt 2, Wnt 5, BMP6, Fz receptor, full length LEF1, and the dominant negative form of LEF1 are related to neoplasia, e.g., carcinogenesis or carcinoma of the liver, prostate, breast, and colon. Accordingly the present invention provides the dominant negative form of LEF1 and methods of using the dominant negative form of LEF1, the full-length LEF1, Wnt2, Wnt5, BMP6, and Fz receptor for detection and treatment of neoplasia, e.g., colon carcinoma, carcinogenesis, or the predisposition thereto.

One embodiment of the present invention provides a dominant negative form of LEF1. A dominant negative form of LEF1 can be any truncated LEF1 that lacks the ability to bind β-catenin or inhibits the activity of the full-length LEF1, e.g., inhibiting its binding activity to β-catenin or its transcription activation activity upon binding to β-catenin. According to the present invention, the dominant negative form of LEF1 is a polypeptide containing the C-terminal sequence of LEF1, e.g., lacking at least 60, 70, 80, 90, 100, or 110 amino acids of the N-terminal sequence of LEF1, which is not adjacent to any amino acid sequence to which it is naturally adjacent. LEF1 includes any LEF1 homolog and can be from any species, e.g., human.

In one aspect, a dominant negative form of LEF1 is a polypeptide containing the C-terminal sequence of LEF1, e.g., from a methionine codon such as the first methionine codon within exon 3 of the LEF1 gene or a polypeptide having an amino acid sequence corresponding to or not substantially different from the sequence of a polypeptide naturally produced by an internal promoter such as the promoter within intron 2 of the LEF1 gene or a homolog or derivative thereof which has substantially the same function.

In another aspect, a dominant negative form of LEF1 is a polypeptide containing the human C-terminal sequence of LEF1, e.g., about 283 amino acids of human C-terminal LEF1 or a C-terminal fragment from about amino acid residue 116 to the C-terminal end of human LEF1.

Another embodiment of the present invention provides polynucleotides encoding the dominant negative form of LEF1 of the present invention. Such polynucleotides can be included in a vector, e.g., an expression vector for expressing the dominant negative form of LEF1 in vitro or in vivo or a vector useful for gene therapy. In one embodiment, a cell is transformed with an expression vector containing the polynucleotides of the present invention.

Another embodiment of the present invention provides an internal promoter of the LEF1 gene, e.g., in a vector. An internal promoter of the LEF1 gene can be any promoter within the LEF1 gene and optionally can include an enhancer within or outside of the LEF1 gene. In one embodiment, the internal promoter is any promoter within the LEF1 gene that produces the dominant negative form of LEF1, e.g., activates the transcription of a LEF1 mRNA beginning from exon 3 of the LEF1 gene. In another embodiment, the internal promoter is the promoter beginning within intron 2 of the LEF1 gene, e.g., including at least 88 nucleotides at the 3' end of intron 2. In yet another embodiment, the internal promoter of the LEF1 gene provided by the present invention is not adjacent to any sequence at its 5' end to which it is naturally adjacent.

The present invention also provides antibodies that specifically bind to the dominant negative form of LEF1 of the present invention or an immunogenic fragment or epitope thereof. The antibodies provided by the present invention can be monoclonal or polyclonal antibodies and can be made by any suitable means known to one skilled in the art. In one embodiment, the antibodies of the present invention specifically bind to the dominant negative form of LEF1 or an immunogenic fragment or epitope thereof and does not specifically bind to the β-catenin binding region of LEF1 or an immunogenic fragment or epitope thereof.

According to another feature of the present invention, the level of the full-length LEF1 and dominant negative form of LEF1 can be used for detecting neoplasia, e.g., colon carcinoma, carcinogenesis, or the predisposition thereto. For example, the present invention provides a method for detecting colon carcinoma, carcinogenesis, or the predisposition thereto by detecting the level of the full-length or dominant negative form of LEF1 in a sample, e.g., a colon tissue sample such as colon mucosal tissue from a subject in need of such testing. An increase in the level of the full-length LEF1 or a decrease in the level of the dominant negative form of LEF1 as compared to the level in a normal sample is indicative of colon carcinoma, carcinogenesis, or the predisposition thereto in the subject, e.g., human.

According to the present invention, colon carcinoma includes, without limitation any malignant growth of colon tissues while colon carcinogenesis includes, without limitation any progression as part of colon carcinoma formation, e.g., occurrence or reoccurrence of colon carcinoma. A predisposition to colon carcinoma or carcinogenesis represents certain chance in the future of becoming colon carcinoma or carcinogenesis.

The level of the full-length LEF1 and dominant negative form of LEF1 can be detected or determined by any suitable means available to one skilled in the art. For example, one could detect the activity, transcription, translation, or the promoter activity level, e.g., at steady state or kinetics for the full-length LEF1 and the dominant negative form of LEF1. Usually the full-length LEF1 is not detectable in normal colon tissue, thus any detection of the full-length LEF1 can be qualified as an increase in the level of the full-length LEF1.

The present invention also provides kits useful for carrying out the detection methods provided by the present invention. A kit useful for detecting neoplasia, e.g., colon carcinoma, carcinogenesis, or predisposition thereto using the methods of the present invention can include a probe for detecting the level of the full-length LEF1 or dominant negative form of LEF1 or both and instructions on how to use the probe to practice the detection methods provided by the present invention. For example, a probe for detecting the activity, transcription, translation, or the promoter activity of the full-length LEF1 or dominant negative form of LEF1 can be included in the kit. Such probe can be a nucleotide probe or monoclonal antibody specific for the full-length LEF1 or dominant negative form of LEF1. In one embodiment, the kit additionally includes a control for the normal level of the full-length LEF1 or dominant negative form of LEF1, e.g, a normal colon tissue sample.

The present invention also provides therapeutic applications of the dominant negative form of LEF1. The dominant negative form of LEF1 of the present invention can be used to inhibit the activity of the full-length LEF1 or treat neoplasia, e.g., colon carcinoma or carcinogenesis. For example, the dominant negative form of LEF1 or its encoding polynucleotides can be introduced to a cell or administered to a subject to treat colon carcinoma or carcinogenesis, in part, by inhibiting or decreasing the activity of the full-length LEF1, e.g., inhibit LEF1's interaction with β-catenin and its activation of the Wnt pathway downstream target genes such as myc, COX-2, ccnd1, MMP7, and TCF7.

According to the present invention, colon carcinoma or carcinogenesis can be treated by any agent that either decreases the level of the full-length LEF1 or increases the level of the dominant negative form of LEF1. Such agent can be any compound or molecule and can affect the activity, transcription, translation, or promoter activity level, either steady state or kinetics, of the full-length LEF1 or the dominant negative form of LEF1. Such agent can be any known agent including, without limitation, the dominant negative form of LEF1 and its encoding polynucleotides or can be any agent to be discovered.

One way of discovering such agent is by using the screening methods provided by the present invention. According to the present invention, one can screen for agents useful for the treatment of colon carcinoma or carcinogenesis by contacting or incubating a test agent with a promoter for the full-length LEF1 or the dominant negative form of LEF1 and detecting the activity of the promoter by any suitable means known to one skilled in the art, e.g., by using a reporter gene. Any test agent that decreases the activity of the promoter for the full-length LEF1 or increases the activity of the promoter for the dominant negative form of LEF1 is indicative of an agent useful for the treatment of colon carcinoma or carcinogenesis.

Alternatively one can screen for such agents by contacting or incubating a test agent with a cell and detecting the level of the full-length LEF1 and dominant negative form of LEF1. Any test agent decreases the level of the full-length LEF1 or increases the level of the dominant negative form of LEF1 is indicative of an agent useful for the treatment of colon carcinoma or carcinogenesis. The changes of the level of the full-length LEF1 and the dominant negative form of LEF1 can be any change including, without limitation, changes of the activity, transcription, translation, or promoter activity level of the full-length LEF1 or the dominant negative form of LEF1.

The agents of the present invention useful for therapeutic treatment can be administered alone, in a composition with a suitable pharmaceutical carrier, or in combination with other therapeutic agents. An effective amount of the agents to be administered can be determined on a case-by-case basis. Factors should be considered usually include age, body weight, stage of the condition, other disease conditions, duration of the treatment, and the response to the initial treatment.

Typically, the agents are prepared as an injectable, either as a liquid solution or suspension. However, solid forms suitable for solution in, or suspension in, liquid vehicles prior to injection can also be prepared. The agent can also be formulated into an enteric-coated tablet or gel capsule according to known methods in the art.

The agents of the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The agents may also be directly applied to tissue surfaces, e.g., during surgery. Sustained release administration is also specifically included in the invention, by such means as depot injections or erodible implants.

According to another aspect of the present invention, neoplasia, e.g., colon carcinoma, carcinogenesis or the predisposition thereto can be detected by measuring the level of Wnt ligands, e.g., Wnt2 or Wnt5 in a sample from a subject, e.g., a sample of human colon tissue. An increase in the level of Wnt 2 or Wnt 5 or both as compared to the level in a normal sample is indicative of neoplasia, e.g., colon carcinoma, carcinogenesis, or the predisposition thereto in the subject. The level of Wnt ligands, e.g., Wnt 2 or Wnt 5 includes without limitation the level of activity, transcription, translation, or promoter activity of Wnt 2 or Wnt 5.

Alternatively neoplasia, e.g., colon carcinoma, carcinogenesis or the predisposition thereto can be detected by measuring the level of members of the TGFβ family of ligands, e.g., BMP6 in a sample from a subject, e.g., a sample of human colon tissue. A decrease in the level of BMP6, e.g., activity, transcription, translation, or promoter activity of BMP6 as compared to the level in a normal sample is indicative of colon carcinoma, carcinogenesis, or the predisposition thereof in the subject.

In another embodiment, the invention provides a method for detecting a cell proliferative disorder of colon tissue by determining the level of BMP-6 expression or activity in a cell suspected of being a cancer cell. The method includes contacting an agent that detects BMP-6 polynucleotide or polypeptide. When the BMP-6 polypeptide is to be detected, anti-BMP-6 antibody is contacted with a cell suspected of having a BMP-6 associated disorder and detecting binding to the antibody. The antibody reactive with BMP-6 is labeled with a compound which allows detection of binding to BMP-6. For purposes of the invention, an antibody specific for BMP-6 polypeptide may be used to detect the level of BMP-6 in biological fluids and tissues. Any specimen containing a detectable amount of antigen can be used. A preferred sample of this invention is colon tissue. The level of BMP-6 in the suspect cell can be compared with the level in a normal cell to determine whether the subject has a BMP-6-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti-hapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

Anti-BMP-6 antibodies can be used in vitro and in vivo to monitor the course of amelioration of a BMP-6-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the BMP-6-associated disease is effective. The term "ameliorate" denotes a lessening of the detrimental effect of the BMP-6-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Thus, where a cell-proliferative disorder is associated with the expression of BMP-6, nucleic acid sequences that interfere with BMP-6 expression at the translational level can be used. This approach utilizes, for example, antisense nucleic acid and ribozymes to block translation of a specific BMP-6 mRNA, either by masking that mRNA with an antisense nucleic acid or by cleaving it with a ribozyme.

The present invention also provides gene therapy for the treatment of cell proliferative or immunologic disorders which are mediated by BMP-6 protein. Such therapy would achieve its therapeutic effect by introduction of the BMP-6 antisense polynucleotide into cells having the proliferative disorder. Delivery of antisense BMP-6 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a BMP-6 sequence of interest into the viral vector, along with another gene which encodes the ligand for a receptor on a specific target cell, for example, the vector is now target specific.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to .PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for BMP-6 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0.mu.m can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

There are a variety of applications using the polypeptide, polynucleotide, and antibodies of the invention, related to colon tissue. Such applications include treatment of cell proliferative disorders. In addition, BMP-6 may be useful in various gene therapy procedures.

Yet another aspect of the present invention provides methods for determining the differentiation level of a neoplasia, e.g. colon carcinoma. In general, the differentiation level of a neoplasia is closely related to the prognosis of the condition. For example, a well differentiated neoplasia, e.g., tumor or cancerous growth has a better prognosis than a poorly differentiated one. According to the present invention, Frizzled (Fz) receptors, e.g., Fz1 and Fz2 can be used as markers to determine the differentiation level of a neoplasia, e.g., colon carcinoma. For example, detection of any Frizzled receptor, e.g., Fz1 or Fz2 is indicative of non-differentiation, poorly differentiated, or not well differentiated neoplasia, e.g., colon carcinoma, which can be associated with a poorer prognosis as compared to a colon carcinoma having no detectable level of Fz receptor. Detection of Fz receptor is also associated with tumor invasion especially an invasion front of a neoplasia. In another embodiment, the invention provides methods of treating colon cancer in a subject in need thereof, the method comprising administering to the subject an effective amount of at least one compound that modulates Fz receptor activity or expression. For example, if it is desirable to reduce Fz receptor expression, various nucleic acid molecules, such as antisense, can be utilized to reduce expression. Further, since it is desirable to eliminate, kill or stunt the growth of a cancer cell, it would be desirable to target an antibody to the Fz receptor, where the antibody is operatively attached to at least a chemotherapeutic agent, radiotherapeutic agent, anti-angiogenic agent, apoptosis-inducing agent, steroid, toxic agent, antimetabolite, anthracycline, vinca alkaloid, anti-tubulin drug, antibiotic, cytokine, alkylating agent or coagulant, for example.

It may also be desirable to modulate Fz receptor activity or expression. The term "modulate" primarily envisions the suppression of a Fz receptor expression when Fz receptor subunit is overexpressed as compared to a control (e.g., a normal or non-cancerous cell). The term "modulate" also includes the augmentation of the expression of a Fz receptor when it is underexpressed or has a decreased activity as compared to a control, such that one of skill in the art can specifically target the receptor with lethal compounds, as discussed below. The term "compound" as used herein describes any molecule, e.g., protein, nucleic acid, peptide, petidomimetic, polypeptide, pharmaceutical, biological agent, antibody, agent or combinatorial or phage display library with the capability of altering the expression or activity of an Fz receptor.

Candidate agents for interfering with expression of Fz receptor include an antisense nucleic acid, ribozymes, and the like. Candidate agents also encompass numerous chemical classes wherein the agent modulates Fz receptor expression or activity. Of particular interest, the invention includes antibody molecules or functional fragements thereof that are targeted to an Fz receptor and that are operatively attached to an agent or compound to be delivered to a cancer cell.

When Fz receptor subunit is overexpressed, candidate agents include antisense nucleic acid sequences. Antisense nucleic acids are DNA or RNA molecules that are complementary to at least a portion of a specific mRNA molecule (Weintraub, 1990, Scientific American, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, 1988, Anal. Biochem., 172:289). In a preferred embodiment where the Fz receptor is overexpressed, the cell is a colon cancer cell.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, Antisense Res. and Dev., 1:227; Helene, 1991, Anticancer Drug Design, 6:569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, J. Amer. Med. Assn., 260:3030). A major advantage of this approach is that, because they are sequence-specific, only mRNAs with particular sequences are inactivated.

There are two basic types of ribozymes namely, tetrahymena-type (Hasselhoff, 1988, Nature, 334:585) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

In yet another embodiment of the invention, there is provided a method of treating cancer in a subject in need thereof, the method including administering to the subject an effective amount of at least one compound that modulates Fz receptor activity or expression. In the case of a subject with colon cancer, for example, it may be desirable to decrease Fz receptor activity or expression. Alternatively, it may be desirable to upregulate Fz receptor activity on the cell surface in order to target a therapeutic molecule to the receptor in order to kill the cell.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition. As used herein, the phrase "preventing disease conditions" refers to preventing a disease, disorder or condition from occurring in a subject who may be at risk for the disease, but has not yet been diagnosed as having the disease.

As used herein, a "subject in need" refers to an individual who has been diagnosed with a disease, disorder, or condition, or who is at risk for a disease, disorder or condition. Those of skill in the art will understand that a variety of methods may be used to determine a subject at risk for a disease, and that whether a subject is at risk for a disease will depend on a variety of factors known to those of skill in the art, including genetic make-up of the subject, age, body weight, sex, diet, general health, occupation, exposure to environmental conditions, marital status, and the like, of the subject.

As used herein, "administering" refers to means for providing a compound that modulates a Fz receptor activity or expression to a patient, using oral, sublingual intravenous, subcutaneous, transcutaneous, intramuscular, intracutaneous, intrathecal, epidural, intraoccular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

As employed herein, the phrase "an effective amount", when used in reference to invention methods employing compounds that modulate Fz receptor activity or expression, refers to a dose of compound sufficient to provide circulating concentrations high enough to impart a beneficial effect on the recipient thereof. An effective amount of a compound may be, for example, an antibody operatively attached to a toxin, which is targeted to the Fz receptor. The specific therapeutically effective dose level for any particular patient will depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. Dosage levels typically fall in the range of about 0.001 up to 100 mg/kg/day; with levels in the range of about 0.05 up to 10 mg/kg/day being more typical.

The term "antibody" is used broadly herein to include polyclonal and monoclonal antibodies, as well as antigen binding fragments of such antibodies. Depending on the particular method of the invention, antibodies having various specificities can be useful, including an antibody, or antigen binding fragment thereof, that specifically binds a polypeptide of the invention.

The term "specifically binds" or "specifically interacts," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity for an FZ polpeptide of the invention epitope are included within the definition of an antibody. The term "specifically binds" or "specifically interacts" is used similarly herein to refer to the interaction of members of a specific binding pair, as in Fz1 or Fz2, for example, and an antibody.

The term "antibody" as used herein includes naturally occurring antibodies as well as non-naturally occurring antibodies, including, for example, single chain antibodies, chimeric antibodies, bifunctional antibodies and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering,* 2d ed. (Oxford University Press 1995)).

An antibody having a desired specificity can be obtained using well known methods. For example, an antibody having substantially the same specific binding activity of H2 can be prepared using methods as described by Liabeuf et al. (supra, 1981) or otherwise known in the art (Harlow and Lane, "Antibodies: A laboratory manual" (Cold Spring Harbor Laboratory Press 1988)).

Where a peptide portion of an Fz ligand or an Fz receptor of the invention, for example, is used as the immunogen is non-immunogenic, it can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1988). Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol.* (1992), section 2.4.1).

Monoclonal antibodies also can be obtained using methods that are well known and routine in the art (Kohler and Milstein, *Nature* 256:495, 1975; Coligan et al., supra, 1992, sections 2.5.1-2.6.7; Harlow and Lane, supra, 1988). For example, spleen cells from a mouse immunized with β2-microglobulin, or an epitopic fragment thereof, can be fused to an appropriate myeloma cell line such as SP/02 myeloma cells to produce hybridoma cells. Cloned hybridoma cell lines can be screened using, for example, labeled Fz polypeptide or antigenic peptide to identify clones that secrete monoclonal antibodies having the appropriate specificity, and hybridomas expressing antibodies having a desirable specificity and affinity can be isolated and utilized as a continuous source of the antibodies. Polyclonal antibodies similarly can be isolated, for example, from serum of an immunized animal. Such antibodies, in addition to being useful for performing a method of the invention, also are useful, for example, for preparing standardized kits. A recombinant phage that expresses, for example, a single chain antibody also provides an antibody that can used for preparing standardized kits.

Monoclonal antibodies, for example, can be isolated and purified from hybridoma cultures by a variety of well established techniques, including, for example, affinity chromatography with Protein-A SEPHAROSE gel, size exclusion chromatography, and ion exchange chromatography (Barnes et al., in *Meth. Mol. Biol.* 10:79-104 (Humana Press 1992); Coligan et al., supra, 1992, see sections 2.7.1-2.7.12 and sections 2.9.1-2.9.3). Methods of in vitro and in vivo multiplication of monoclonal antibodies are well known. For example, multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody-producing tumors. Optionally, the animals can be primed with a hydrocarbon, for example, an oil such as pristane (tetramethylpentadecane) prior to injection. After one to three weeks, the desired monoclonal antibody is recovered from the body fluid of the animal.

An antigen binding fragment of an antibody can be prepared by proteolytic hydrolysis of a particular antibody such as H2, or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. No. 4,036,945 and U.S. Pat. No. 4,331,647; Nisonhoff et al., *Arch. Biochem. Biophys.* 89:230. 1960; Porter, *Biochem. J.* 73:119, 1959; Edelman et al., *Meth. Enzymol.,* 1:422 (Academic Press 1967); Coligan et al., supra, 1992, see sections 2.8.1-2.8.10 and 2.10.1-2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of variable heavy ($V_H$) chains and variable light ($V_L$) chains, which can be a noncovalent association (Inbar et al., *Proc. Natl. Acad. Sci., USA* 69:2659, 1972). Alternatively, the variable chains can be linked by an intermolecular disulfide bond or cross-linked by chemicals such as glutaraldehyde (Sandhu, *Crit. Rev. Biotechnol.* 12:437, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are well known (see, for example, by Whitlow et al., "Methods: A Companion to Methods in Enzymology" 2:97, 1991; Bird et al., *Science* 242:423-426, 1988; Ladner et al., U.S. Pat. No. 4,946,778; Pack et al., *Bio/Technology* 11:1271-1277, 1993; Sandhu, supra, 1992).

Another example of an antigen binding fragment of an antibody is a peptide coding for a single complementarity determining region (CDR). CDR peptides can be obtained by constructing polynucleotides encoding the CDR of an antibody of interest. Such polynucleotides can be prepared, for example, using the polymerase chain reaction to synthesize a variable region encoded by RNA obtained from antibody-producing cells (see, for example, Larrick et al., *Methods: A Companion to Methods in Enzymology* 2:106, 1991, which is incorporated herein by reference).

In another embodiment, the invention provides a method for identifying a compound which modulates Fz receptor activity. The method includes: a) incubating components comprising the compound and Fz receptor or polynucleotide encoding the receptor under conditions sufficient to allow the components to interact; and b) determining the effect of the compound on Fz activity or expression, respectively, before and after incubating in the presence of the compound. Compounds that affect Fz activity or expression include peptides, nucleic acid molecules (e.g., antisense), peptidomimetics, polypeptides, chemical compounds and biologic agents. Fz activity or expression can be assayed using methodology as described in the present Examples.

Incubating includes conditions which allow contact between the test compound and the Fz receptor or polynucleotide. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008-1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229-237, 1988).

The invention includes antibodies immunoreactive with FZ polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and F(ab')$_2$, Fv and SCA fragments which are capable of binding an epitopic determinant on FZ.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as a FZ polypeptide, to which the paratope of an antibody, such as an FZ-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing FZ-specific antibodies include FZ polypeptides or FZ polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of Fz. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-FZ immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., non-specific) antibodies of the same class or subclass (isotype) as those used in the assays (e.g., IgG1, IgG2a, IgM, etc.) can be used as "blockers". The concentration of the "blockers" (normally 1-100 ug/ul) may be important, in order to maintain the proper sensitivity yet inhibit any unwanted interference by mutually occurring cross reactive proteins in the specimen.

In using a monoclonal antibody for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the FZ antigen for which the monoclonal antibodies are specific. The concentration of detectably labeled monoclonal antibody which is administered should be sufficient such that the binding to those cells having FZ is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m2 to about 500 mg/m2, preferably 0.1 mg/m2 to about 200 mg/m2, most preferably about 0.1 mg/m2 to about 10 mg/m2. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are 111In, 97Ru, 67Ga, 68Ga, 72As, 89Zr, and 201Ti.

A method of the invention can be performed by administering an Fz receptor or an inhibitor of Fz activity or expression, and one or more agents to a subject. The agents can be diagnostic agents, nutritional molecules, toxins, therapeutic agents, radiomodulating agents, or combinations thereof. For example, a method of the invention can be performed by administering a Fz antibody and one or more therapeutic agents such as a combination of cancer chemotherapeutic agents used to treat a particular type of cancer. In addition, the agent, or one or all of a combination of agents, can be contained in an encapsulating medium such as a liposome, which can be a modified liposome such a stealth liposome or other "masked" liposome. Anti-cancer agents encapsulated in the liposome includes carcinostatic agents such as adriamycin, daunomycin, mitomycin, cisplatin, vincristine, epirubicin, methotrexate, 5Fu, and aclacinomycin, toxins such as ricin A and diphtheria toxin, and antisense RNA. Encapsulation of anti-cancer agent into liposome is accomplished by hydration of the lipids with an aqueous solution of the anti-cancer agent. Adriamycin, daunomycin, and epirubicin may be encapsulated into a liposome by means of remote loading method taking advantage of pH gradient (Lawrence D. M. et al., Cancer Research 49 5922, 1989).

A method of the invention can be performed using a diagnostic agent, which is detectable external to the subject, thus providing a means for performing in vivo diagnostic imaging, for example, to identify the presence of a cancer in a subject. For such a method, a diagnostic agent such as a gamma ray emitting radionuclide, for example, indium-111 or technitium-99, or gadolinium-containing liposomes, can be administered with a Fz receptor antibody to a subject, and can be detected using a solid scintillation detector. Similarly, a positron emitting radionuclide such as carbon-11 or a paramagnetic spin label such as carbon-13 can be coadministered with a Fz receptor antibody and can be detected using positron emission transaxial tomography or magnetic resonance imaging, respectively. Such methods can identify a primary tumor as well as a metastatic lesion, which may not be detectable using other methods, and can detect other pathologic conditions having a vascular component.

The invention thus provides a range of conjugated antibodies and fragments thereof in which the antibody is operatively attached to at least a first therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Attachment of agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr) into the primary sequence of the antibody.

Currently, agents for use in anti-Fz receptor antibody therapeutic conjugates and related methods and uses are those that complement or enhance the effects of the antibody and/or those selected for a particular tumor type or patient. Therapeutic agents that complement or enhance the effects of the antibody include radiotherapeutic agents, anti-angiogenic agents, apoptosis-inducing agents and anti-tubulin drugs, any one or more of which are preferred for use herewith.

The attachment or association of the preferred agents with anti-Fz receptor antibodies gives "immunoconjugates", wherein such immunoconjugates often have enhanced and even synergistic anti-tumor properties. Currently preferred anti-angiogenic agents for use in this manner are angiostatin, endostatin, any one of the angiopoietins, vasculostatin, canstatin and maspin. Currently preferred anti-tubulin drugs include colchicine, taxol, vinblastine, vincristine, vindescine and one or more of the combretastatins.

The use of anti-cellular and cytotoxic agents results in anti-Fz receptor "immunotoxins", whereas the use of coagulation factors results in anti-Fz "coaguligands". The use of at least two therapeutic agents is also contemplated, such as combinations of one or more radiotherapeutic agents, anti-angiogenic agents, apoptosis-inducing agents, anti-tubulin drugs, anti-cellular and cytotoxic agents and coagulation factors.

In certain applications, the anti-Fz therapeutics will be operatively attached to cytotoxic, cytostatic or otherwise anti-cellular agents that have the ability to kill or suppress the growth or cell division of endothelial cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle.

Exemplary chemotherapeutic agents include: steroids; cytokines; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan. Indeed, any of the agents disclosed herein in Table C could be used. Certain preferred anti-cellular agents are DNA synthesis inhibitors, such as daunorubicin, doxorubicin, adriamycin, and the like.

In certain therapeutic applications, toxin moieties will be preferred, due to the much greater ability of most toxins to deliver a cell killing effect, as compared to other potential agents. Therefore, certain preferred anti-cellular agents for anit-Fz receptor antibody constructs are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; a-sarcin; aspergillin; restrictocin; ribonucleases, such as placental ribonuclease; diphtheria toxin and pseudomonas exotoxin.

Preferred toxins are the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

For tumor targeting and treatment with immunotoxins, the following patents and patent applications are specifically incorporated herein by reference for the purposes of even further supplementing the present teachings regarding anti-cellular and cytotoxic agents: U.S. application Ser. Nos. 07/846,349; 08/295,868 (U.S. Pat. No. 6,004,554); Ser. No. 08/205,330 (U.S. Pat. No. 5,855,866); Ser. No. 08/350,212 (U.S. Pat. No. 5,965,132); Ser. No. 08/456,495 (U.S. Pat. No. 5,776,427); Ser. No. 08/457,487 (U.S. Pat. No. 5,863,538); Ser. Nos. 08/457,229 and 08/457,031 (U.S. Pat. No. 5,660,827) and Ser. No. 08/457,869 (U.S. Pat. No. 6,051,230).

The anti-Fz receptor antibody of the present invention may be linked to an anti-tubulin drug. "Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization.

Currently preferred anti-tubulin drugs for use herewith are colchicine; taxanes, such as taxol; vinca alkaloids, such as vinblastine, vincristine and vindescine; and combretastatins. Exemplary combretastatins are combretastatin A, B and/or D, including A-1, A-2, A-3, A-4, A-5, A-6, B-1, B-2, B-3, B-4, D-1 and D-2 and prodrug forms thereof.

The anti-Fz receptor therapeutics may comprise a component that is capable of promoting coagulation, i.e., a coagulant. Here, the targeting antibody may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the Gla modification; Russell's viper venom Factor X activator; platelet-activating compounds, such as thromboxane A2 and thromboxane A.2 synthase; and inhibitors of fibrinolysis, such as alpha2-antiplasmin.

Tumor targeting and treatment with coaguligands is described in the following patents and patent applications, each of which are specifically incorporated herein by reference for the purposes of even further supplementing the present teachings regarding coaguligands and coagulation factors: U.S. application Ser. Nos. 07/846,349; 08/205,330 (U.S. Pat. No. 5,855,866); Ser. No. 08/350,212 (U.S. Pat. No. 5,965,132); Ser. Nos. 08/273,567; 08/482,369 (U.S. Pat. No. 6,093,399); Oct. 20, 1998); Ser. Nos. 08/485,482; 08/487,427 (U.S. Pat. No. 6,004,555); Ser. No. 08/479,733 (U.S. Pat. No. 5,877,289); Ser. Nos. 08/472,631; and 08/479,727 and 08/481,904 (U.S. Pat. No. 6,036,955).

The preparation of immunoconjugates and immunotoxins is generally well known in the art (see, e.g., U.S. Pat. No. 4,340,535, incorporated herein by reference). Each of the following patents and patent applications are further incorporated herein by reference for the purposes of even further supplementing the present teachings regarding immunotoxin generation, purification and use: U.S. application Ser. Nos. 07/846,349; 08/295,868 (U.S. Pat. No. 6,004,554); Ser. No. 08/205,330 (U.S. Pat. No. 5,855,866); Ser. No. 08/350,212 (U.S. Pat. No. 5,965,132); Ser. No. 08/456,495 (U.S. Pat. No. 5,776,427); Ser. No. 08/457,487 (U.S. Pat. No. 5,863,538); Ser. Nos. 08/457,229 and 08/457,031 (U.S. Pat. No. 5,660,827) and Ser. No. 08/457,869 (U.S. Pat. No. 6,051,230).

In the preparation of immunoconjugates and immunotoxins, advantages may be achieved through the use of certain linkers. For example, linkers that contain a disulfide bond that is sterically "hindered" are often preferred, due to their greater stability in vivo, thus preventing release of the toxin moiety prior to binding at the site of action. It is generally desired to have a conjugate that will remain intact under conditions found everywhere in the body except the intended site of action, at which point it is desirable that the conjugate have good "release" characteristics.

Depending on the specific toxin compound used, it may be necessary to provide a peptide spacer operatively attaching the anti-Fz receptor antibody and the toxin compound, wherein the peptide spacer is capable of folding into a disulfide-bonded loop structure. Proteolytic cleavage within the loop would then yield a heterodimeric polypeptide wherein the antibody and the toxin compound are linked by only a single disulfide bond.

When certain other toxin compounds are utilized, a non-cleavable peptide spacer may be provided to operatively attach the anti-Fz receptor antibody and the toxin compound. Toxins that may be used in conjunction with non-cleavable peptide spacers are those that may, themselves, be converted by proteolytic cleavage, into a cytotoxic disulfide-bonded form. An example of such a toxin compound is a Pseudomonas exotoxin compound.

A variety of chemotherapeutic and other pharmacological agents can also be successfully conjugated to anti-Fz receptor antibody therapeutics. Exemplary antineoplastic agents that have been conjugated to antibodies include doxorubicin, daunomycin, methotrexate and vinblastine. Moreover, the attachment of other agents such as neocarzinostatin, macromycin, trenimon and (alpha-amanitin has been described (see U.S. Pat. Nos. 5,660,827; 5,855,866; and 5,965,132; each incorporated herein.)

Antibodies or chemical entities created to recognize Fz receptors are used to carry elements to image Fz receptor expressing or secreting cancer cells and locate the disease. These antibodies or chemical entities are included in the term biological binding unit, which term is used to refer to patient compatible entities which bond to Fz and comprise antibodies or their derivatives, molecular recognition units and peptides. Antibodies encompass monoclonal and polyclonal antibodies and their derivatives and fragments and include single chain antibodies, bifunctional antibodies and other antibody constructs. Further, these biological binding units may deliver particle emitting radionuclides, drugs or toxins to promote a therapeutic effect. For example, a peptide ligand created to recognize Fz receptors delivering 188 Re to the tumor site thereby delivers localized radiation to ablate the disease.

By way of a further example, a peptide may be developed that binds to Fz receptors and competitively inhibits the natural ligand(s) for the Fz receptor, but not able to activate the receptor itself. This peptide may be produced on a commercially available synthesizer, using FMOC solid phase chemistry. In one application, either tyrosine, lysine, or phenylalanine is included in the peptide to which an N2 S2 chelate is complexed as per U.S. Pat. No. 4,897,255. The anti-FZ peptide conjugate is then combined with a radiolabel, for example, either sodium 99m Tc pertechnetate (Na99m TcO4) or sodium 188 Re perrhenate(Na188 ReO4) and may be used to locate a Fz receptor-producing tumor.

The invention also provides the use of anti-Fz antibodies covalently combined with radioactive, cytotoxic or chemotherapeutic molecules and considers using these antibodies in immunoabsorption procedures to separate benign from malignant cells. Further, the concept of passive immunotherapy with antiidotypic antibodies is now possible.

This invention includes a method for detecting and locating neoplasia associated with one or more Fz receptors, e.g., colon cancer in vivo by injecting a human subject parenterally with an entity that has been constructed to target Fz receptor(s), that is either a polyclonal or monoclonal antibody, or fragments thereof, or constructs thereof including, but not limited to, single chain antibodies, bifunctional antibodies, molecular recognition units, and peptides or entities that mimic peptides, where the tumour targeting agent is labelled either directly, or indirectly with a chelating agent, with one 131 I, 125 I, 123 I, 111 In, 99m Tc, 90 Y, 188 Re, 153 Sm, 67 Ga, 32 P, 201 Tl, 77 Br or 18 F and is imaged with a photoscanning device, or where the tumor targeting agent is labelled with either gadolinium, terbium, tin, iron or isotopes thereof and attached covalently to create a paramagnetic conjugate for the purpose of magnetic resonance imaging. A further application of the radioimaging technique is in the field of radioimmunoguided surgery, whereby a hand-held scintigraphic probe detector enables a surgeon to identify and remove localized metastatic disease.

These entities which are constructed to target Fz receptors, as aforementioned, can also deliver a toxic agent for therapeutic purposes against colon cancer, where the toxic agent is a radioisotope that emits Auger electrons, and/or alpha particles, and/or beta particles, and/or neutrons, and/or other sub-atomic particles, or toxic compounds including but not limited to, diphtheria toxin, ricin toxin, adriamycin, chlorambucil, or daunorubicin. Further toxins which can be used are ricin and its derivatives and fragments, Monensin, Verrucarin A, Abrin and its derivatives, Vinca alkaloids, Tricothecenes, and Pseudomonas exotoxin A. Further drugs for use as toxic agents are as follows: Leucovorin, Folinic acid, Methotrexate, Mitomycin C, Neocarzinostatin, Vinblastine, Mitomycin, Melphalan, Mechlorethamine, Fluorouracil, Fluoxuriding, Idarubicin, Doxorubicin, Epirubicin, Cisplatin, Carmustine, Cyclophosphamide, Bleomycin, Vincristine and Cytarabine.

A list of radioisotopes, which can be used for treating colon cancers, is as follows: 277 Ac, 211 At, 131 Ba, 77 Br, 109 Cd, 51 Cr, 67 Cu, 165 Dy, 155 Eu, 153 Gd, 198 Au, 166 Ho, 113m In, 115m In, 123 I, 125 I, 131 I, 189 Ir, 191m Ir, 192 Ir, 194 Ir, 52 Fe, 55 Fe, 59 Fe, 177 Lu, 109 Pd, 32 P, 226 Ra, 186 Re, 188 Re, 153 Sm, 46 Sc, 47 Sc, 72 Se, 75 Se, 105 Ag, 89 Sr, 35 S, 177 Ta, 177m Sn, 121 Sn, 166 Yb, 169 Yb, 90 Y, 212 Bi, 119 Sb, 197 Hg, 97 Ru, 100 Pd, 10im Rh, 212 Pb.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

β-Catenin-Sensitive Isoforms of Lymphoid Enhancer Factor-1 are Selectively Expressed in Colon Cancer LEF1 Gene is Selectively Expressed During Colon Carcinogenesis.

We and others have shown by Northern analysis that the LEF1 gene is often expressed in colon cancer cell lines whereas it is not detectable in normal colon tissue (Porfir B., et al., *Oncogene*, 15:2833-39 (1997) and Korinek V., et al., *Science*, 275:1784-87 (1997)). Here we used in situ hybridization to determine if LEF1 expression occurs in primary colon cancer tissue from patient biopsies and to determine if it is expressed in a small population of normal colon cells in crypts. Since the LEF/TCF family member TCF4 is expressed in normal colon (Korinek V., et al., *Science*, 275: 1784-87 (1997)), we used human TCF4 probes as a reference. In situ hybridization with digoxigenin-labeled sense and antisense RNA complementary to the 3' untranslated regions of human LEF1 or TCF7L2 mRNA were used as probes to detect endogenous messages in colon tissue. In striking contrast to TCF4, we did not detect LEF1 mRNA in normal mucosal tissue, not even in minor subpopulations of cells in the crypts of colon (FIG. 1*a-j*). However, we detected LEF1 mRNA in all colon carcinoma biopsies analyzed (10 out of 10. FIG. 1*k-n*). We conclude that within the limits of detection for in situ hybridization, the LEF1 gene is not expressed in any cell in normal colon tissue but is aberrantly activated during colon carcinogenesis.

LEF1 Isoform.

Figure 2:
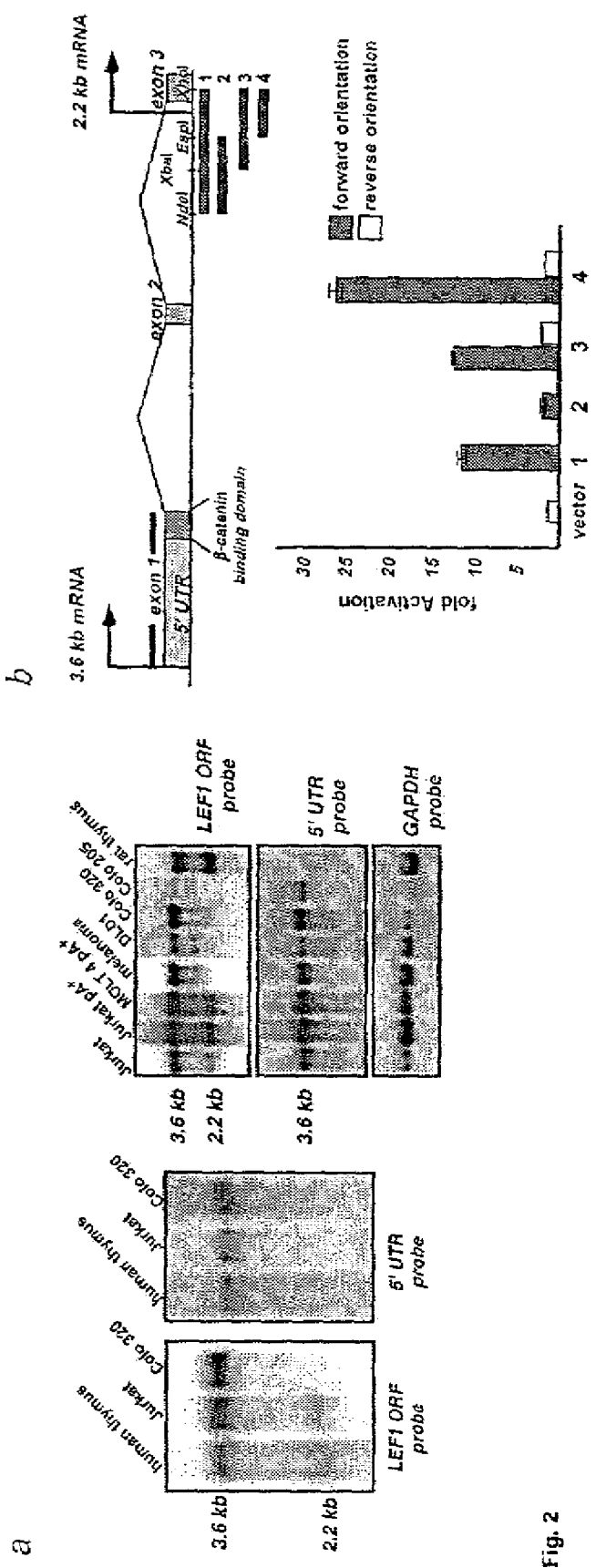
FIG. 2 shows the activity of a promoter in intron 2 of LEF-1. Fragments from the second intron of LEF1 were tested for promoter activity in Jurkat T lymphocytes using the pGL2 luciferase reporter plasmid. A 232 nucleotide fragment (EspI-XhoI) can act as a promoter for transcription in the forward but not the reverse orientation. Luciferase light units varied from 500 to 15,000. Data are derived from duplicate samples, and the results shown represent one of four replicative experiments. Fold activation was calculated as a ratio of luciferase levels from each reporter construct relative to the promoter-less pGL2 plasmid (vector). A schematic of exons 1-3 shows the relative positions of the introns, promoters and coding sequences for the LEF1 β-catenin binding domain.

In normal thymus tissue, two mRNAs of 3.6 kb and 2.2 kb are produced from LEF1 (refs. 12, 13). However, in colon cancer and melanoma cells only the 3.6 kb mRNA is present (FIG. 2A). Previously we determined that the 3.6 kb mRNA contains 1.2 kb 5' and 3' untranslated regions and a 1.2 kb open reading frame encoding a full length LEF1 polypeptide with β-catenin and HMG DNA binding domains (Hovanes, K., et al., *Nucleic Acids Res.*, 28:1994-2003 (2000)). Here we probe the structure of the 2.2 kb mRNA by Northern analysis (FIG. 2A). Whereas probes from the LEF1 open reading frame and 3' UTR could hybridize to both 3.6 and 2.2 kb mRNAs, we could not detect the 2.2 kb mRNA with a probe from exon 1 (FIG. 2A). Extensive screening of cDNA libraries and other methods such as 5' RACE did not uncover any evidence for alternative splicing to generate a smaller 2.2 kb mRNA, therefore we considered the possibility of a second, downstream promoter.

Figure 3:
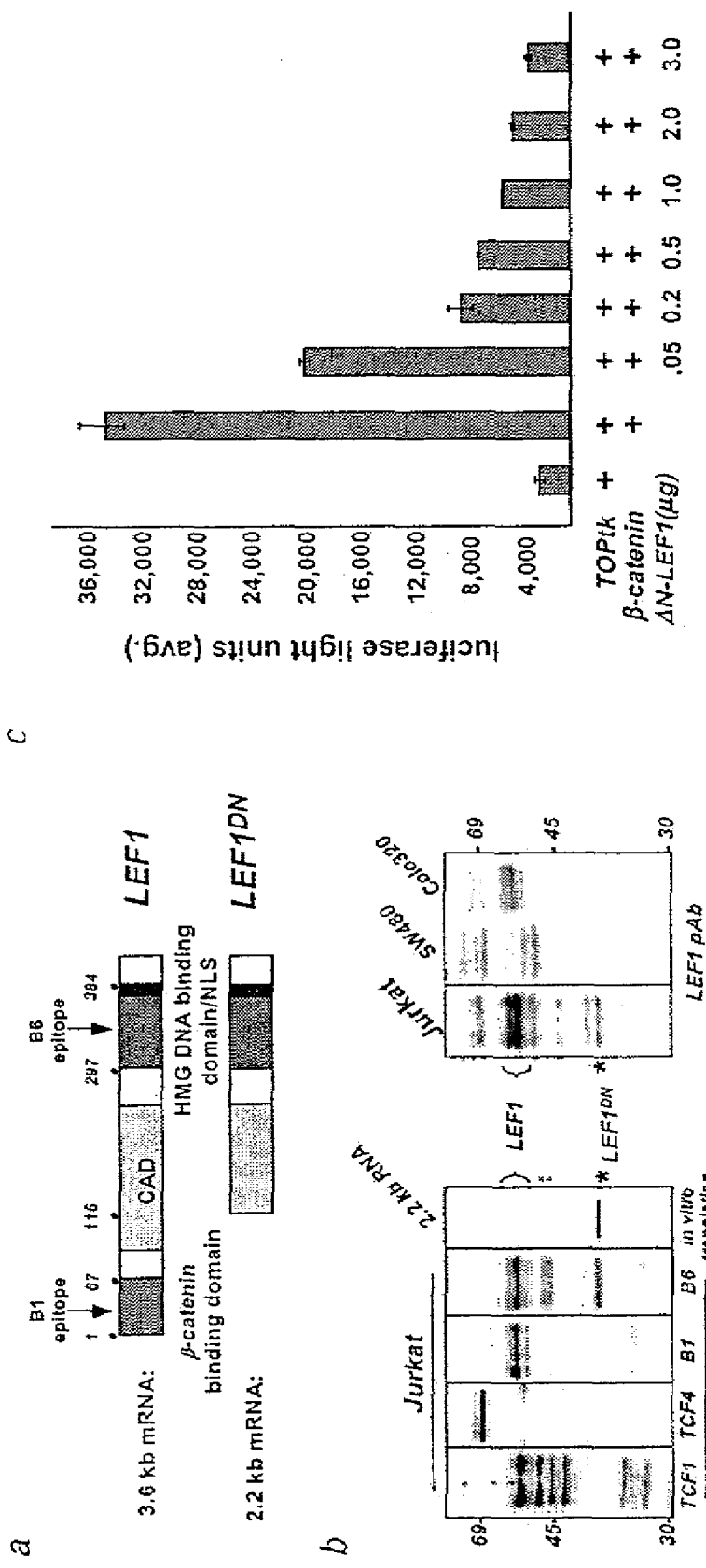
FIG. 3A, B and C show that LEF1 produces two different protein products that differ at the N-terminus.
FIG. 3B Jurkat T lymphocytes, but not colon cancer cells express LEF1DN. Whole cell extracts (50,000 cell equivalents) were analyzed on western blots probed with monoclonal antibodies specific for full-length LEF1 (REMB1, Exalpha Biologicals), and TCF4 or TCF1 proteins (Upstate Biotech). REMB6 (Exalpha Biologicals) is a monoclonal antibody raised against LEF1 protein, but recognizes an epitope in the HMG box that is highly conserved in LEF/TCF family members. Polyclonal LEF1 antisera recognizes conserved epitopes in all mammalian LEF/TCF family members and isoforms. TCF polypeptides that cross-react with REMB6 and LEF1 polyclonal antibody are indicated by●. A polypeptide of 38 kD (LEF1DN; asterisk) is detected by the LEF1 polyclonal antisera and REMB6 but not REMB1 and therefore matches the predicted structure of LEF1DN. A 2.2 kb in vitro transcribed RNA produces a single 38 kD LEF1DN product in rabbit reticulocyte lysates. Lanes 1-3 contain whole cell lysates from Jurkat T lymphocytes as a reference for the whole cell lysate from normal human peripheral blood lymphocytes in lane 4. Full-length LEF1 polypeptides are indicated in whole cell extracts from Jurkat cells and the colon cancer cells SW480 and Colo320 (75,000 cell eciuivalents). LEF1DN is only detected in Jurkat extract and is not present in the extracts from colon cells. c, LEF1DN can repress activation of reporter gene expression by θ-catenin. The LEF/TCF reporter plasmid TOPtk was co-transfected into 2017 T lymphocytes with increasing amounts of an expression vector for DNLEF, a truncated form of LEF1 similar in structure to LEF1DN (a.a. 67-399) (ref. 22). Endogenous LEF/TCFs in Jurkat cells are able to work with b-catenin to activate the reporter gene 15-fold, but in the presence of DNLEF1, activation is reduced to basal levels.

The exon and intron structure of human LEF1 and TCF1 are highly similar and both genes express similar sets of isoforms (Hovanes, K., et al., *Nucleic Acids Res.*, 28:1994-2003 (2000); Van de Wetering M., et al., *J. Biol. Chem.*, 267;8530-36 (1992); and Van de Wetering, M., et al., *Mol. Cell. Biol.*, 16:745-52 (1996)). Although TCF1 produces only one detected mRNA on Northern blots, a second promoter in intron 2 drives expression of an additional, similarly sized mRNA encoding a truncated TCF1 isoform that does not have the β-catenin binding domain[15]. We searched introns 1 and 2 of LEF1 for regions containing a promoter and detected activity with fragments of the second intron when they were cloned into a luciferase reporter vector in the forward but not the reverse direction (XbaI-XhoJ, EspI-XhoI, FIG. 2B). Within the smallest of these fragments is a consensus TATA box motif 50 nucleotides 5' of the third exon. Promoter activity is destroyed when we delete these 50 nucleotides. The predicted protein product from this second promoter is a 283 amino acid polypeptide beginning at a methionine codon within exon 3 (amino acid 116 within full length LEF1 and is thus missing the β-catenin binding domain and crucial amino acids in the context-dependent activation domain (CAD, FIG. 3A). We mapped the transcription start site within the second promoter, and a 2.2 kb RNA beginning at this +1 position and including all downstream exons was generated for in vitro translation. A single 38 kD polypeptide was produced in this reaction (asterisk, FIG. 3B). Using LEF1 polyclonal antisera for western analysis, we detected a 38 kD polypeptide in extracts from Jurkat T lymphocytes that express 3.6 kb and 2.2 kb LEF1 mRNAs but not in extracts of SW480 or Colo320 colon cancer cells that express only the 3.6 kb mRNA (LEF1 pAb. FIG. 3B). We also used LEF1, TCF1 and TCF4 specific monoclonal antibodies to confirm that this polypeptide is a product of LEF1 and contains the HMG DNA binding domain but not the β-catenin binding domain (REMB1, REMB6, TCF1, TCF4, FIG. 3B).

Dominant Negative LEF1 Truncated Isoforms.

Overexpression of this truncated LEF1 isoform represses the ability of β-catenin to activate reporter gene expression (ΔN-LEF1, FIG. 3C). Repression must occur because the truncated LEF1 protein can bind to the LEF/TCF sites and prevent β-catenin recruitment to the target reporter plasmid. Therefore, the 38 kD LEF1 protein may function as a natural antagonist for Wnt signaling and hereafter shall be referred to as LEF1DN for "dominant negative". The structure of LEF1$^{DN}$ is similar to a truncated TCF1 isoform that can function as a dominant negative to suppress activation of reporter genes by full length TCF proteins (Korinek V., et al., *Science*, 275:1784-87 (1997) and Morin P., et al., *Science* 275:1787-90 (1997)). Expression of dominant negative forms of LEF/TCFs may be a general feature of LEF/TCF loci used to moderate the effects of Wnt signaling by competing with full length LEF/TCFs for target gene occupancy.

Figure 1:
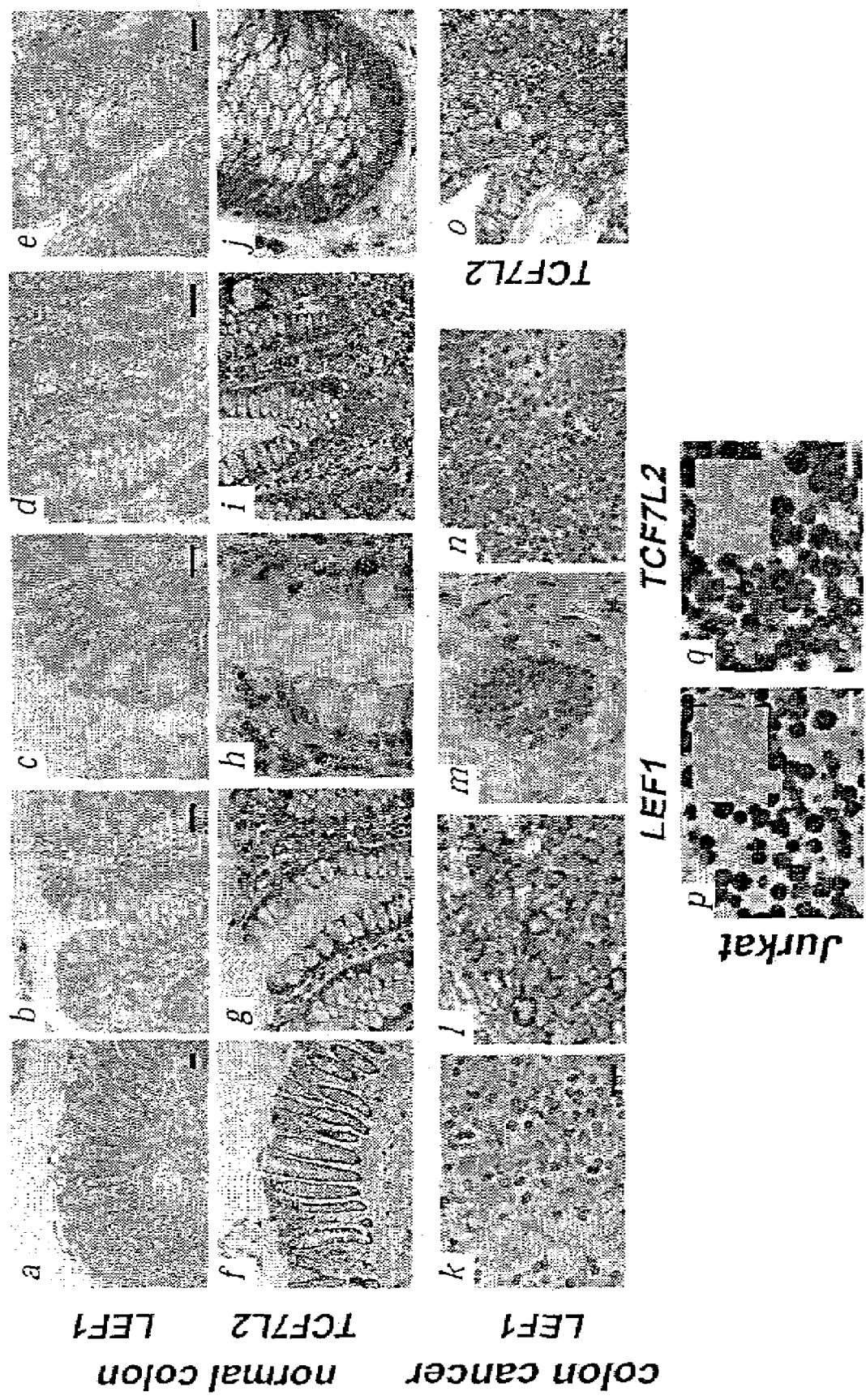
FIG. 1 shows LEF1 and TCF7L2 (gene for TCF4 protein) expression in normal human colon tissue and human colon carcinomas. In situ hybridization with digoxigenin-labeled sense and antisense RNA complementary to the 3' untranslated regions of human LEF1 or TCF7L2 mRNA were used as probes to detect endogenous messages in colon tissue. LEF1 mRNA (a-e), is not expressed whereas TCF7L2 mRNA (f-j), is highly expressed in normal colon tissue. Both LEF1 and TCF7L2 expression are detected in human colon carcinomas. Expression was detected in 10 of 10 colon carcinoma samples each derived from separate patients (k-o). Detection is specific as antisense, but not sense RNA probes (inset) detect high level expression of LEF1 and TCF7L2 in Jurkat T cells (p, q). Magnification for a, f is 10× (size bar is 100 mm), for b, d, g, i is 40× (size bar is 10 mm). and for c, e, h, i, k-q is 100× (size bar is 10 mm).

Since no LEF1 mRNA is detected in normal colon tissue, expression in cancer must be due to inappropriate activation of the first LEF1 promoter. We tested whether β-catenin/TCF complexes regulate the LEF1 promoter because it is known that Wnt3a can induce expression of chLEF1 in chick limb buds (Kengaku M., et al., *Science*, 280:1274-77 (1998)) and because genetic activation of the Wnt pathway has been observed in most spontaneous colon cancers (Kinzler K., et al., *Cell*, 87:159-70 (1996); Polakis, *Genes and Dev.*, 141837-51 (2000); and Roose J., et al., *Biochem. Biophys. Acta.*, 1424:M23-37 (1999)). We observed that co-transfection of expression vectors for full length TCF1 or TCF4 and β-catenin with a luciferase reporter gene driven by the LEF1 promoter caused a seven-fold and 4.6-fold activation of luciferase expression respectively (FIG. 4A). Activation was dependent on 3-catenin because co-transfection with Δ19 β-catenin, a mutant that cannot bind to LEF/TCFs (ref. 19), did not allow activation (FIG. 4A). We used DNAase I footprinting and recombinant LEF1 protein to identify two LEF/TCF binding sites at +192 and +283 relative to the LEF1 transcription start site. Partially fractionated whole cell extracts from Jurkat T lymphocytes, which express high levels of TCF1, TCF4 and LEF1, protected sequences over the +283 site suggesting that this is a high affinity LEF/TCF binding site. When we deleted this footprinted region (to +262), β-catenin activation of the promoter was reduced from 9.2-fold to 4-fold; when both downstream footprints were deleted, β-catenin activation of the promoter was nearly eliminated (FIG. 4B). Thus, TCF1 or TCF4 together with β-catenin can activate the LEF1 promoter through one or two response elements that lie in an unusual position downstream of the transcription start site. We also observed that β-catenin/TCF complexes can activate the LEF1$^{DN}$ promoter in intron 2, but to a modest level. Clearly, additional factors or epigenetic mechanisms must modulate the ability of the Wnt pathway to access the LEF1 promoter but not the LEF1 promoter in colon cancer. To test the model that LEF1 expression is regulated by β-catenin/TCF complexes in colon cancer cells, we co-transfected a GFP/APC (Green Fluorescent Protein/Adenomatous Polyposis Coli) expression plasmid with the LEF1 promoter luciferase reporter construct into SW480 cells (FIG. 4C). This APC fusion protein has previously been shown to reduce β-catenin protein in SW480 cells, and indeed we observed a three-fold decrease in LEF1 promoter activity (FIG. 4C, 1.0 µg GFP/APC). There is no inhibition with the parent GFP expression plasmid but instead a modest increase in luciferase levels (*Figure* 4C). We also overexpressed GFP/APC in Colo320 cells, which produce higher detectable levels of LEF1 protein on western blots, and observed a decrease of β-catenin and LEF1 levels, but no detectable decrease of TCF4 protein (FIG. 4C). We conclude that the LEF1 promoter is sensitive to the level of β-catenin in the nucleus of colon cancer cells, and thus is likely to be a Wnt gene target.

Although the current model for colon cancer predicts a correlation between colon tumorigenesis and high levels of LEF/TCF target gene expression, removal of one of these target genes from mice—the Tcf1 locus itself—leads to the development of adenomas in the gut and mammary glands (Roose J., et al., *Science*, 285:1923-26 (1999)). It has been suggested that loss of Tcf1 reflects loss of the putative tumor suppressor properties of the smaller dominant negative form of TCF1 which must be present in levels that exceed those of full-length TCF1 and TCF4 and therefore TCF1 is a candidate gene for loss of heterozygosity (LOH) in human colon cancer (Roose J., et al., *Science*, 285:1923-26 (1999)). However, given our results that the highly similar LEF1 locus has two promoters that are differentially regulated in colon cancer, we believe that promoter misregulation at the TCF1 locus is an alternative to TCF1 LOH. The promoter for dominant negative TCF1 could be down-regulated or shut off in cancer and the promoter that drives expression of full-length, β-catenin binding forms could be up-regulated, or turned on. Expression of full length LEF1 and TCF1 in the absence of the moderating influence of their dominant negative isoforms allows for the large pool of -catenin protein to be fully exploited for target gene activation. LEF1/β-catenin complexes have been shown to transform normal chicken embryo fibroblasts (Aoki M., et al., *Proc. Natl. Acad. Sci. USA*, 96:139-44 (1999)) We believe that in addition to providing insight into the mechanism of tumor progression, these genes can be used as important markers of Wnt-stimulated progression of carcinogenesis.

Materials and Methods:

In situ Hybridization. We performed in situ hybridization of 5 mm sections from paraffin-embedded tissue of normal and malignant colon biopsy samples as described ("Non-radioactive In situ Hybridization"; Roche Molecular Biochemicals) with modifications (T. Milovanovic, T. Truong, and J. L. Marsh). Human TCF4 and LEF1 cDNAs encoding the 3' untranslated regions were used to generate single-stranded antisense RNA with digitonin-conjugated UTP nucleotides. Probes were hybridized to tissue for 72 hours, then washed and incubated with alkaline phosphatase-conjugated anti-digoxigenin antibody (Roche) for one hour at 37° C. We developed tissues with 5-bromo-4-chloro-3-indolyl-phosphate and 4-nitroblue tetrazolium chloride (BCIP/NBT; Roche), and used a 0.1% Fast Red solution for counterstain. All antisense and sense probes were tested for specificity on human Jurkat T lymphocyte cells which express both LEF1 and TCF4. The sense probes did not produce any detectable signal. Signals were visualized with an Olympus B50 microscope with Nomarski optics and photographs were captured with digital technology within 48 hours of hybridization.

Northern Analysis. We analyzed LEF1 expression by Northern analysis of 10 μg of total or 1 μg of polyA+ RNA as described previously (Porfiri E., et al., *Oncogene*, 15:2833-39 (1997)). The LEF1 ORF probe was generated by StyI digestion (nt#821-1894), and the 5' UTR probe was generated by BglII digestion (nt#2-761). Melanoma RNA was purified from A2058 cells from a human metastatic melanoma (ATCC# 11147-CRL).

Transient Transfection Assays. We subcloned fragments of intron 2 by the indicated enzymes and cloned them in both orientations into the SmaI site of pGL2-Enhancer plasmid (Promega). We transfected 5 μg of each promoter construct with 0.5 μg of CMV-LacZ reporter plasmid into 2017 T lymphocytes. Cell lysates were prepared for luciferase and β-galactosidase assays 20 hours post-transfection (Hovanes K., et al., *Nucleic Acids Res.*, 28:1994-2003 (2000)). To test for dominant negative activity of a truncated LEF1 protein, we co-transfected ΔNLEF1 (aa67-399) with 1 μg of the TOPtk reporter plasmid (gift of Dr. H. Clevers, Univ. Utrecht) and 0.5 μg of CMV-LacZ. To assay for β-catenin regulation of the LEF1 promoter, we co-transfected 2 μg of TCF1 and TCF4 expression plasmids with a luciferase reporter plasmid driven by the LEF1 promoter (B5: −672, +305; ref. 14) and 4 μg of wild type or mutant Δ19 β-catenin expression plasmids into 2017 cells (Prieve M. G., et al., *Mol. Cell. Biol.*, 19:4503-15 (1999)). SW480 cells (250,000/35 mm well) were transfected using Effectene (Qiagen; manufacturer's protocols) and 0.5 μg of the B5 LEF1 promoter/luciferase reporter plasmid with 0.1 μg CMVLacZ and the indicated amounts of GFP/APC. Colo320 cells (500,000/35 mm well) were transfected with Effectene and the indicated amounts of GFP/APC expression vector. Whole cells were harvested 24 hours later for western analysis.

Western Analysis. We separated proteins from 50,000 Jurkat cells or 75,000 colon cancer cells by SDS-PAGE electrophoresis and probed blots of these gels with the indicated antibodies. TCF1 and TCF4 monoclonal antibodies (Upstate Biotechnology) were used at a 1:1000 dilution to identify cross-reacting polypeptides detected by REMB6 and LEF1 polyclonal antisera. The REMB1 LEF1 monoclonal (Exalpha) was used at a 1:5000 dilution and REMB6 (Exalpha; detects all LEF/TCFs) at a 1:500 dilution. LEF1 polyclonal rabbit antisera (which also detects all LEF/TCF proteins) was used at a 1:1000 dilution. β-catenin levels were analyzed by monoclonal antisera from Transduction Laboratories (1:1000 dilution).

DNAase I Footprinting. Partially purified recombinant LEF1 (10 μg) and Jurkat and HeLa whole cell extracts (50 μg) were used in standard DNAase I footprinting assays as previously described Hovanes K., et al., *Nucleic Acids Res.*, 28:1994-2003 (2000)). The LEF1 promoter was labeled with (Carlsson P., et al., *Genes Dev.*, 7:2418-30 (1993)) P at a phosphatased HindIII site in the polylinker region of B5 plasmid between the promoter and luciferase coding sequences.

Accession Numbers. The nucleotide sequence of the second intronic promoter has been submitted to Genbank (AF288570). The AF288570 submission also contains part of exon 3 (nucleotides 202 to 284), including a short stretch of coding sequence. Genbank AF288571 lists the nucleotide sequence of the human LEF1 cDNA and amino acid sequence of LEF1.

EXAMPLE 2

Expression of Wnt Ligands and Frizzled Receptors in Colonic Mucosa and in Colon Carcinoma Materials and Methods Tissue Acquisition. Archived, paraffin-embedded, pathologic specimens were obtained under an IRB-approved protocol (UCI98-20) following oral and written informed consent. Patients were identified through the Chao Family Comprehensive Cancer Center as individuals with recent surgical resection of colonic adenocarcinoma. Samples of normal colonic tissue as well as colon cancer tissue were obtained from different cuts of the same surgical specimen for each patient. When possible, histologically normal and malignant tissues were included on a single slide to allow for direct comparison of staining intensity. Over 20 patients with colon cancer for whom tissue blocks were available were enrolled on this study.

Cell Lines. Human cell lines were obtained from ATCC (American Type Culture Collection, Manassas, Va.). They included: Jurkat, an acute T-cell leukemia cell line utilized as a control for in situ hybridizations which was maintained in culture in RPMI1640 media with 10% fetal bovine serum (FBS); HT-29, an adherent colorectal adenocarcinoma cell line which forms well differentiated adenocarcinomas in nude mice and is maintained in culture in DMEM media with 10% FBS; Colo205, a free-floating colorectal adenocarcinoma cell line maintained in RPMI1640 media with 10% FBS; CaCo2, an adherent colorectal adenocarcinoma cell line which forms moderately well differentiated adenocarcinoma in nude mice and is maintained in culture in DMEM media with 20% FBS; PANC1, an adherent epithelioid pancreatic cancer cell line maintained in culture in DMEM media with 10% FBS. For in situ hybridization and antibody staining controls, cells were pelleted by centrifugation, embedded in paraffin, sectioned, and prepared similarly to tissue samples as described below. To better define the cellular localization of RNA by in situ hybridization, adherent cells (HT29 and CaCo2) were also grown directly on slides (Nunc Lab-Tek II chamber slide), fixed, and prepared for staining. Eliminating paraffin embedding markedly reduces artifacts caused by deparaffinization.

In situ RNA Hybridization. Slides were deparaffinized with sequential xylene/alcohol/dH$_2$O washes and hybridized with single stranded anti-sense RNA probes generated from cDNAs using T7 and T3 RNA polymerase promoters in the respective vectors. Probes were labeled with digoxigenin, hydrolyzed, and hybridized to tissue sections in a moisture-controlled environment at 37° C. for 72 hours at conditions optimized for each probe. Positive hybridization was detected using anti-digoxigenin conjugated to alkaline phosphatase to allow visualization with an alkaline phosphatase substrate. All slides were counterstained lightly for 5 seconds with a hematoxylin-eosin reagent to permit visualization of tissue architecture. Probes for Wnts and BMPs generally included nonhomologous coding sequences or 3' untranslated sequences. Samples from over 20 individuals with colon cancer were analyzed for expression though every sample was not utilized for each probe. Each probe was tested against a minimum of 3 samples of normal and malignant tissue from different patients. Most probes were hybridized against between 10 and 15 separate tissue sections.

Several controls were utilized for every experiment. First, each tissue was subjected to hybridization with either trefoil factor or thymidine kinase probes to ensure that the tissue was preserved adequately to permit in situ RNA hybridization. Trefoil factor and thymidine kinase (TK) are differentially expressed in normal colonic mucosa (the former in goblet cells and the latter in the crypts but not the villi). Trefoil factor is frequently overexpressed in colon carcinoma cells and TK is overexpressed in rapidly proliferating tissues. As a negative control, all tissues were also analyzed with an identical probe in the sense orientation to ensure that there was no detectable staining and to confirm the absence of non-specific hybridization. A panel of cell lines was utilized as additional positive and negative controls. Expression of each gene was defined for each cell line by Northern blot analysis. Cell lines were then centrifuged, embedded in paraffin and sectioned to mimic conditions utilized for tissue samples. Each probe was tested against a panel of control cell lines to ensure reproducibility and precision when compared to Northern blot analyses prior to utilization in tissue sections. Probe was prepared fresh and each lot was subjected to a full battery of positive and negative control testing. This battery of positive and negative controls allowed for extensive quality control as follows: 1) tissue which did not exhibit distinct staining with thymidine kinase or trefoil factor was discarded in order to eliminate tissues with extensive RNA degradation, presumably occurring at the time of surgery prior to fixation, 2) each batch of probe was tested initially against control (+) and (−) cell lines to insure adequacy of probe preparation, 3) each analysis of patient tissue included slides stained with anti-digoxigenin and alkaline phosphatase reagents in order to ensure that background staining was minimal, and 4) each analysis of patient tissue included slide for which a sense RNA probe was utilized in order to ensure that background staining was minimal.

Direct visualization with an Olympus B50 microscope system with Nomarski optics and digital capture technology was utilized to define expression. Photographs of tissue and cell line sections are obtained within 48 hours of completion of the hybridization to minimize slide artifacts that can appear over time. Probes utilized for in situ hybridization included Wnt1, Wnt2, Wnt4, Wnt5a, Wnt5b, Wnt6, Wnt7a, Wnt7b, Wnt10b, BMP2a and BMP6 obtained from Genome Systems. The genes and the accession and identification numbers from the Image consortium are listed: Wnt2, AA970688, 1579015; Wnt-4, AI139742, 1710594; Wnt-5A, W49672, 324901; Wnt-5B, AI201930, 1859198; Wnt-6, AI127113, 1708122; Wnt-7A, AI040985, 1641787; Wnt-7B, AA991310, 1608881; Wnt10B, AI144467, 1708905; BMP2A, AA515983, 925036; BMP6, AA573738, 1012778. Wnt 11 and BMP4 probes were contaminated with T1 phage and were not available from Genome Systems.

Antibody Staining. Paraffin-embedded samples of normal colon and colon cancers were obtained as described above. Normal colon from 15 different patients, as well as >5 distinct samples of well-differentiated and >5 distinct samples of poorly-differentiated colon cancer were analyzed. Polyclonal goat anti-human Fz1+2 antibodies, which react with both human Fz1 and Fz2 cell surface receptors, were obtained from Santa Cruz Biotechnology (Santa Cruz, Calif.). Samples were deparaffinized with xylene/ethanol and incubated with primary antibody (2 ug/ml) for 30 minutes at 25° C. This was followed by incubation with biotinylated donkey-anti-goat secondary antibody (1ug/ml) and subsequently with horseradish peroxidase and DAB chromogen. Donkey serum was utilized as a blocking agent to reduce background staining. Negative controls included slides hybridized with secondary antibody and HRP/DAB chromagen but without primary (anti-Fz) antibody. Additional controls performed with each experiment included staining of paraffin-embedded cell lines known to express Fz.

Wnt2 and Wnt5 are Expressed in Colon Cancer.

In situ hybridization was performed on both normal and malignant paraffin-embedded tissues using digoxigenin-labeled antisense RNA probes, along with negative and positive controls to ensure adequacy of the tissue and probes and absence of non-specific background hybridization, as outlined in Materials and Methods. Paraffin-embedded cell lines served as controls for each probe and clearly distinguished positive hybridization from negative, sense probe, hybridization. Comparisons of normal tissue to malignant tissue on different regions of the same slide ensured identical treatment of tissues for comparison of expression.

Examination of patient samples showed that most Wnt ligands were expressed in both the normal colonic mucosa and in colon cancer (Table 1).

TABLE 1

Expression of Wnts, BMPs and Fz in human tissues and colon cancer cell lines.

| | Normal colonic mucosa | Colon Cancer | Ht29 | Colo205 | CaCo2 | Panc1* |
|---|---|---|---|---|---|---|
| Wnt 1 | + | + | + | + | + | |
| Wnt 2 | − | etero@ + | Weakly + | Weakly + | + | |
| Wnt 4 | + | + | + | + | + | |
| Wnt 5A | +, stronger at base of crypts | Strongly + | + | + | + | |
| Wnt 5b | + | Hetero + | + | + | + | |
| Wnt 6 | + | + | + | + | + | |
| Wnt 7a | −, possible few + cells at base | − | Weakly + | Weakly + | − | |
| Wnt 7b | + | + | + | Weakly + | Hetero + | |
| Wnt 10b | + | + | + | + | + | |
| BMP 2a | − | − | Weakly hetero + | Weakly hetero + | Weakly hetero + | + |
| BMP6 | + | − to weakly + | + | + | + | |
| Fz ½ | − | +, poorly differentiated | + | + | + | |

*Panc1 cells were utilized as a positive control for BMP2a only.
@Hetero indicates heterogeneous staining among cells visualized in the tissue samples.
Wnt & BMP mRNA were detected by in situ hybridization and Fz ½ protein by immunoperoxidase.

Quantitation of expression was graded as negative (no cells staining), weakly positive (faint staining), positive (evident staining) and strongly positive. In addition, tissue samples which had some cells positive but others within the same specimen negative were graded as heterogeneous in addition to quantitative grading. If one or more specific tissue locations were positive (ie, base of a crypt) but others were not, this information was also recorded. Abundant expression of Wnt1, Wnt4, Wnt5b, Wnt6, Wnt7b and Wnt10b was seen in both normal and malignant tissue and in all three colon cancer cell lines tested. Wnt7a message was absent, or at least below the level of detection, in the colon tissues and only weakly expressed in HT29 and Colo205. Expression of Wnt7a was not seen in CaCO2 cells. Interestingly, Wnt2 was the only ligand that was specifically activated in colon cancer as compared to the expression seen in normal colonic mucosa (Table 1). Specifically, Wnt2 expression was absent in the colonic crypts or villi but was significantly expressed in colon cancer and in the colon cancer cell lines tested. Expression of Wnt5a was noted in the normal colon, with slightly higher signals at the base of the crypt. Wnt Sa expression was slightly stronger in cancerous tissues but the proportional increase compared to normal tissues was less evident than for Wnt2.

Expression of two bone morphogenetic proteins, BMP2a and BMP6, was also evaluated. Significant BMP6 expression was apparent in the normal colonic mucosa and in HT29, Colo205 and CaCO2 but was markedly reduced in the malignant colon cancer tissues (Table 1). In contrast, minimal expression of BMP2a could be detected in normal colon, colon cancer, or any of the colon cancer cell lines. Panc1, a transformed pancreatic adenocarcinoma cell line, was utilized as a positive control because it is known to express BMP2a (Kleff J., et al., Gastroenterology, 116:1202-16 (1999)). Therefore, at least one member of the TGFβ family of ligands is significantly downregulated in human colon cancer.

The expression of Fz1 and Fz2 protein was evaluated with a polyclonal antibody that reacts with these two members of the Fz receptor family. While the expression patterns of different Wnt ligands may direct different cell behaviors, the expression patterns of the Fz receptors are equally important in influencing cell growth. No expression of Fz1/2 could be detected in normal colonic mucosa or in well differentiated colon cancers from 6 independent patient samples. Repeated attempts were made to detect potentially low levels of Fz1/2, but no expression was detected. These results are in marked contrast to the expression of Fz1/2 in samples from 3 patients with poorly differentiated colon cancer. Not only was Fz1/2 expression readily detectable, but was greatest in areas where tumor cells were invading adjacent tissues (the "invasion front"). Each of the colon cancer cell lines tested, HT29, Colo205 and CaCO2, exhibited strong expression of Fz1/2 following immunoperoxidase-based staining on paraffin-embedded sections.

Alterations in the Wnt signaling pathway are involved in colon cancer carcinogenesis in patients with familial polyposis and in the vast majority of patients with sporadic colon cancer (Groden J., et al., Cell, 66:589-600 (1991); Kinzler K. W., et al., Science, 253:661-65 (1991); and (Nagase H., et al., Hum. Mutat., 2:425-34 (1993)). The role of APC mutations in this process, and the resultant accumulations of cytoplasmic and nuclear, pro-oncogenic, β-catenin, are well described (Polakis P., Genetics & Development, 9:15-21 (1999) and Bienz M., et al., Cell, 103:311-20 (2000)). Inactivating mutations in APC, and activating mutations in β-catenin, mimic stimulation of the Wnt pathway leading to increases in cellular β-catenin and changes in downstream target gene expression. Other possible targets facilitating initiation of Wnt pathway activation are the Wnt genes and Fz receptor themselves. The data presented here demonstrate that regulation of expression for several members of the Wnt ligand family and for specific Fz receptors is key to the process of colon carcinogenesis.

In Drosophila and other model organisms, Wnt signaling regulates expression of the ligand and receptor genes in an autoactivating loop and essentially any cell is capable of responding to ligand if given the opportunity (Marsh J. L., et al., Cell & Development Biology, 10:365-75 (1999); Dierick H., et al., Development Biology, 43:153-90 (1999); Baker N. E., Development, 103:289-98 (1998) Baker N. E., Development, 102:489-97 (1998); and Noordermeer J., et al., Development, 116:711-19 (1992)). We had initially hypothesized that one or more specific Wnts would exhibit expression that was localized to the base of the adult human colonic crypt where the population of proliferating stem cells resides, as also postulated by Bienz and Clevers (Bienz M., et al., *Cell,* 103:311-20 (2000)). Surprisingly, we find that expression of the majority of Wnt ligands is rather ubiquitous in both normal and malignant colon and that minimal expression differences can be ascertained between the colonic crypts and villi. Only Wnt2, and to a lesser degree Wnt5a, appear to be upregulated in the transition between normal and malignant mucosa. Only Wnt5a displays any degree of graded expression between the colonic crypts and villi. The colonic crypts contain proliferating mucosal stem cells that give rise to differentiated, non-proliferating mucosal cells that migrate toward the villi (Wong W. M., et al., *J Clin Path.,* 52:321-33 (1999)). In the mouse, TCF4 is required to maintain the proliferative integrity of the undifferentiated crypt stem cell (Korinek V., et al., *Nature Genet.,* 19:379-83 (1998)). We found no evidence for localized expression for the Wnts tested here. Our current data support an alternative model that any restriction of Wnt signaling in the colon is achieved by restricting other components of the Wnt signal transduction pathway, a notable departure from the strategies employed by Drosophila, Xenopus and other model systems.

In accordance with this alternative model of Wnt signal regulation, Fz expression is highly regulated in the human colon. There is little or no apparent expression in normal colon or well differentiated cancers with the Fz1/2 specific antibody utilized in this study. This raises the possibility that Wnt ligands are signaling through a Fz receptor other than Fz1/2 (there are at least 10 human Fz receptors) or through another type of receptor that has yet to be defined. In striking contrast to the lack of detectable Fz1/2 in normal mucosa and well differentiated colon cancer, abundant Fz expression is seen in poorly differentiated cancers, particularly at the invasion front. Other studies have detected nuclear accumulation of β-catenin most prominently at the leading edges of colon tumors (Brabletz T., et al., *Pathol Res Pract.,* 194:701-04 (1998)), a localization pattern that correlates with aggressive tumor invasion (Miyazawa K., et al., *Vichows Arch.,* 437:508-13 (2000)). Transcriptional activation of Fz gene expression may result from high levels of nuclear β-catenin/LEF-TCF complexes in these cells. Studies in human and other model systems provide some evidence for similar autocrine feedback loops within the Wnt/Wingless pathway (Roose J., et al., *Science,* 285:1923-26 (1999); Lescher B., et al., *Dev Dyn.,* 213:440-51 (1998); Cadigan K. M., et al., *Cell,* 93:767-77 (1998); Hooper J. E., et al., *Nature,* 372.461-64 (1994); and Yoffe K. B., et al., *Dev Biol.,* 170:636-50 (1995)). Alternatively, the expression of cell surface Fz receptors at the invasion front may be the primary cause of the increased nuclear accumulation of β-catenin. Perhaps APC mutations alone are not sufficient to drive nuclear β-catenin accumulation to high levels; other processes ongoing at the invasion front may synergize with a crippled APC-dependent degradation pathway to promote the formation of nuclear β-catenin/LEF-TCF complexes. Particularly for the process of tumor invasion, our data suggest that regulation of Fz receptor expression may be more significant than regulation of Wnt ligand expression, whereas in Drosophila the expression of Fz receptors and Wg ligands, are equally critical for normal growth and development (Noordermeer J., et al., *Development,* 116:711-19 (1992) and Muller H., et al., *Development,* 126:577-86 (1999)).

BMPs appear to function in opposition to Wnts in both Drosophila and other model systems (Brook W. J., et al., *Science,* 273:1373-77 (1996); Teisen H., et al., *Development,* 122:3939-48 (1996); Baker J. C., et al., *Genes Dev.,* 13:3149-59 (1999); Heslip T. R., et al., *Development,* 124:1069-78 (1997); and Hirsinger E., et al., *Development,* 124:4605-14 (1997)). Loss of transduction of TGF-β signals mediated by genetic inactivation of the transcription factor Smad4 is thought to be a frequent and important genetic alteration that can promote carcinogenesis in the colon (Moskaluk C. A., *Biochem. Biophys. Acta.,* 1288:M31-33 (1996) and Riggens G. J., et al., *Nature Genet.,* 13:347-49 (1996)). Our data teach that downregulation of BMP6 occurs in colon cancer, when compared to expression in same-individual, normal mucosal controls. If the concept of antagonistic activities of the Wnt and BMP pathways holds in the human colon, it is possible that upregulation of the Wnt pathway, e.g. increased Wnt2 and Fz expression, might lead to increased repression of BMP6 expression or, alternatively, that loss of TGFβ/BMP signaling might lead to upregulation of Wnt pathway genes.

The data presented here teach that Wnt and Fz expression are important in the progression from normal colonic mucosa to a malignant, and invasive, phenotype.

Although the invention has been described with reference to the presently preferred embodiment, it should be understood that various modifications can be made without departing from the spirit of the invention. Accordingly, the invention is limited only by the following claims.

What is claimed is:

1. An isolated DNA molecule comprising a nucleic acid sequence encoding a dominant negative (LEF1$^{DN}$) form of LEF-1 form encoded by SEQ ID NO:1, wherein the LEF1$^{DN}$ lacks the N-terminal 115 amino acid residues of LEF-1, and represses the ability of full-length LEF-1 protein and a β-catenin to activate a reporter gene, and wherein the LEF1$^{DN}$ consists of amino acids 116-399 of SEQ ID NO:2.

2. The isolated molecule of claim 1, further comprising in operable linkage an LEF-1 promoter which is contained in a 232 nucleotide EspI-XhoI fragment of the nucleic acid sequence of in SEQ ID NO:3.

3. An isolated DNA molecule having regulatory activity and comprising a LEF-1 promoter which is contained in a 232 nucleotide EspI-XhoI fragment of the nucleic acid sequence of in SEQ ID NO:3 operably linked to a sequence heterologous to the nucleic acid encoding full length LEF-1.

4. The isolated DNA molecule of claim 3, wherein the isolated DNA molecule comprises nucleotides 13-250 of SEQ ID NO:3.

5. The isolated DNA molecule of claim 3, wherein the heterologous sequence encodes a marker.

6. The isolated DNA molecule of claim 5, wherein the marker is green fluorescent protein or luciferase.

7. A vector comprising the isolated DNA molecule of claim 1.

8. The vector of claim 7, wherein the vector is an expression vector.

9. An isolated host cell comprising the vector of claim 7.

10. An isolated host cell comprising the vector of claim 8.

11. A method for producing LEF1$^{DN}$ comprising:
a) culturing the host cell of claim 10 in culture medium;
b) recovering the LEF1$^{DN}$ from the culture medium; and
c) purifying the LEF1$^{DN}$ from the culture medium.

12. A vector comprising the isolated DNA molecule of claim 3.

13. The vector of claim 12, wherein the vector is an expression vector.

14. An isolated host cell comprising the vector of claim 12.

15. An isolated host cell comprising the vector of claim 13.

16. A method for producing a protein encoded by the heterologous sequence comprising:
   a) culturing the host cell of claim 15 in culture medium;
   b) recovering the protein from the culture medium; and
   c) purifying the protein from the culture medium.

* * * * *